(12) United States Patent
Gerecht-Nir et al.

(10) Patent No.: US 7,947,499 B2
(45) Date of Patent: May 24, 2011

(54) METHOD OF DYNAMICALLY CULTURING EMBRYONIC STEM CELLS

(75) Inventors: Sharon Gerecht-Nir, Haifa (IL); Joseph Itskovitz-Eldor, Haifa (IL)

(73) Assignee: Technion Research & Development Foundation Ltd., Haifa (IL)

( * ) Notice: Subject to any disclaimer, the term of this patent is extended or adjusted under 35 U.S.C. 154(b) by 796 days.

(21) Appl. No.: 10/536,439

(22) PCT Filed: Nov. 30, 2003

(86) PCT No.: PCT/IL03/01017
§ 371 (c)(1),
(2), (4) Date: Nov. 28, 2005

(87) PCT Pub. No.: WO2004/050826
PCT Pub. Date: Jun. 17, 2004

(65) Prior Publication Data
US 2006/0148078 A1    Jul. 6, 2006

Related U.S. Application Data

(60) Provisional application No. 60/429,574, filed on Nov. 29, 2002.

(51) Int. Cl.
*C12N 5/00* (2006.01)

(52) U.S. Cl. ........ 435/394; 435/383; 435/377; 435/375; 435/325

(58) Field of Classification Search .......................... None
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,642,120 A | 2/1987 | Nevo et al. | |
| 4,666,828 A | 5/1987 | Gusella | |
| 4,683,202 A | 7/1987 | Mullis | |
| 4,801,531 A | 1/1989 | Frossard | |
| 4,879,219 A | 11/1989 | Wands et al. | |
| 5,011,771 A | 4/1991 | Bellet et al. | |
| 5,192,659 A | 3/1993 | Simons | |
| 5,272,057 A | 12/1993 | Smulson et al. | |
| 5,281,521 A | 1/1994 | Trojanowski et al. | |
| 5,437,998 A | 8/1995 | Schwarz et al. | |
| 5,464,764 A | 11/1995 | Capecchi et al. | |
| 5,487,992 A | 1/1996 | Capecchi et al. | |
| 5,716,411 A | 2/1998 | Orgill et al. | |
| 5,763,279 A * | 6/1998 | Schwarz et al. | 435/383 |
| 5,843,780 A | 12/1998 | Thomson | |
| 6,090,622 A | 7/2000 | Gearhart et al. | |
| 6,602,711 B1 * | 8/2003 | Thomson et al. | 435/378 |
| 2004/0096967 A1 | 5/2004 | Gryseels et al. | |
| 2004/0121460 A1 * | 6/2004 | Lumelsky et al. | 435/366 |

OTHER PUBLICATIONS

Itskovitz-Eldor et al, Biotechnology Bioengineering, May 2002, vol. 78, No. 4, pp. 442-453.*
McClanahan et al, Blood, 1993, vol. 81, pp. 2903-2915.*
International Preliminary Examination Report Dated May 17, 2006 From the International Preliminary Examining Authority Re.: Application No. PCT/IL03/01017.
Office Action Dated Oct. 30, 2008 From the Israeli Patent Office Re.: Application No. 168773.

* cited by examiner

*Primary Examiner* — Allison M Ford

(57) ABSTRACT

The present invention is of a method of dynamically generating human embryoid bodies which can be used for generating lineage specific cells and cell lines. Specifically, the present invention can be used to generate ESC-differentiated cells for cell-replacement therapy.

13 Claims, 15 Drawing Sheets
(6 of 15 Drawing Sheet(s) Filed in Color)

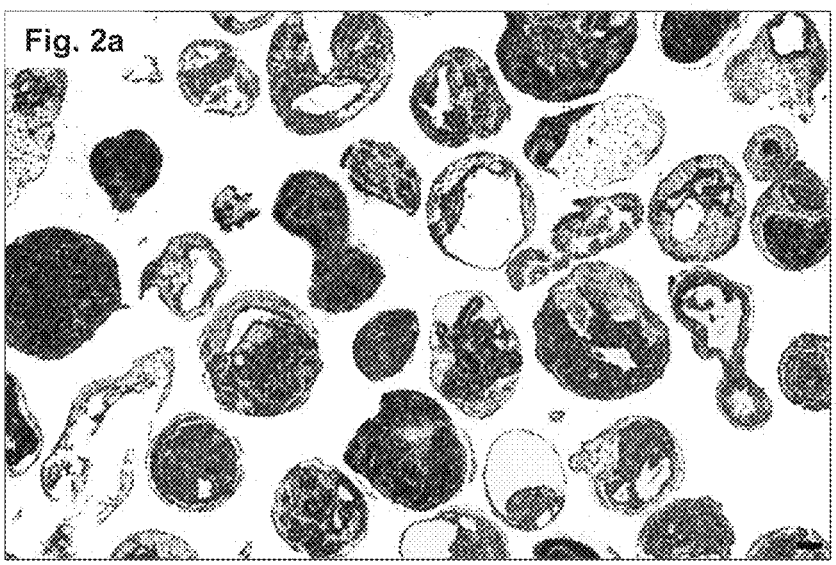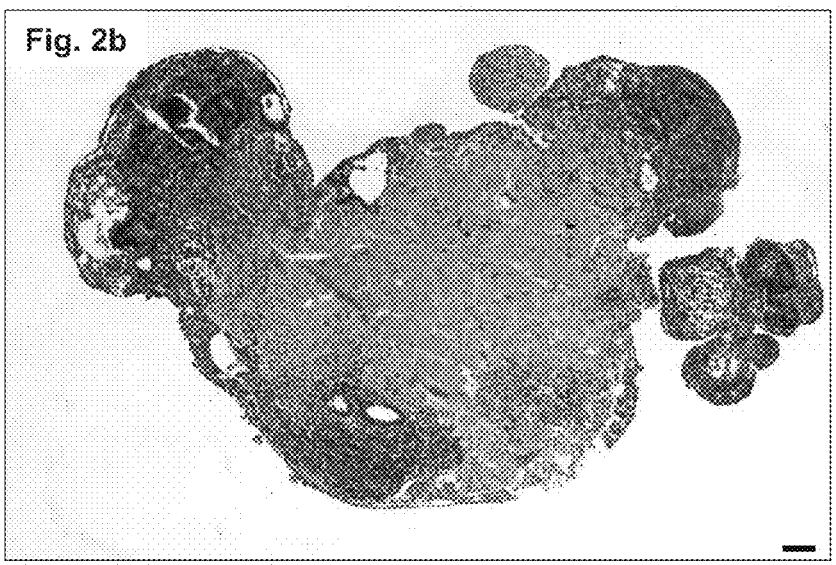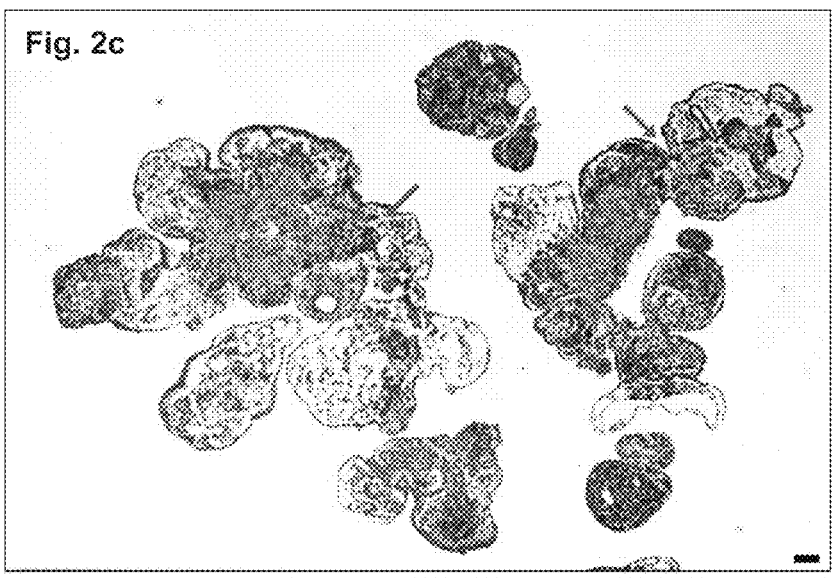

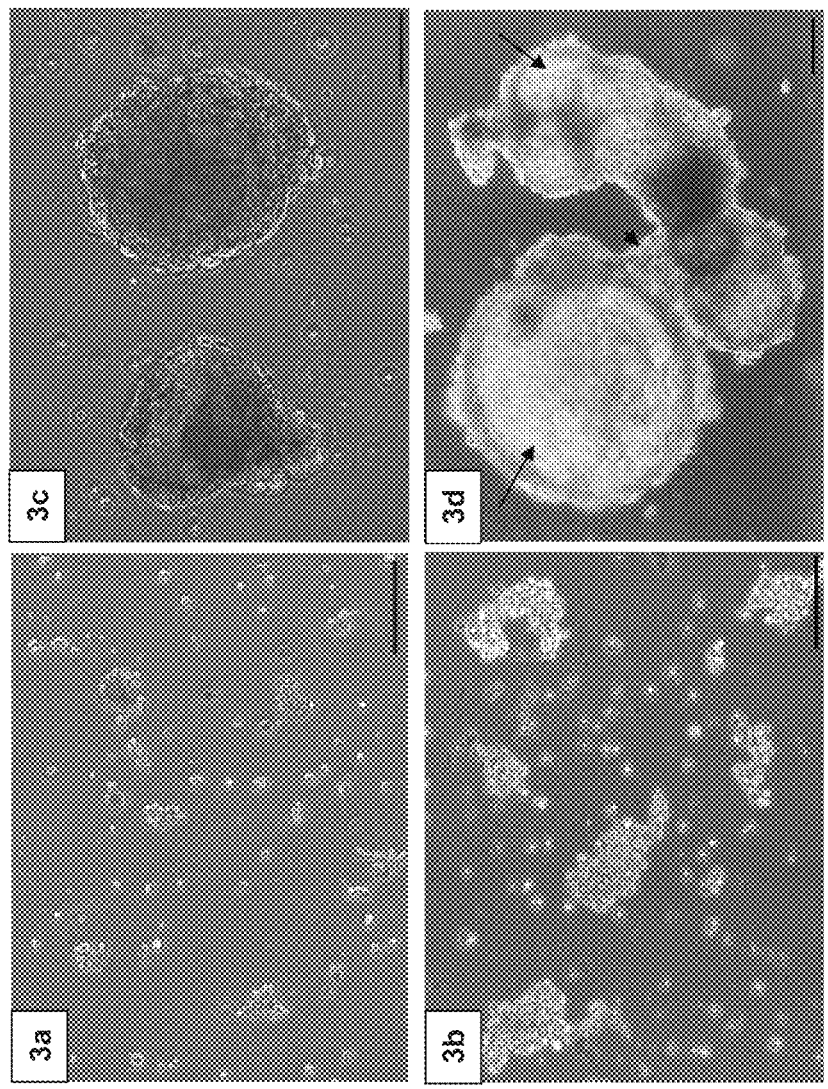
Figs. 3a-d

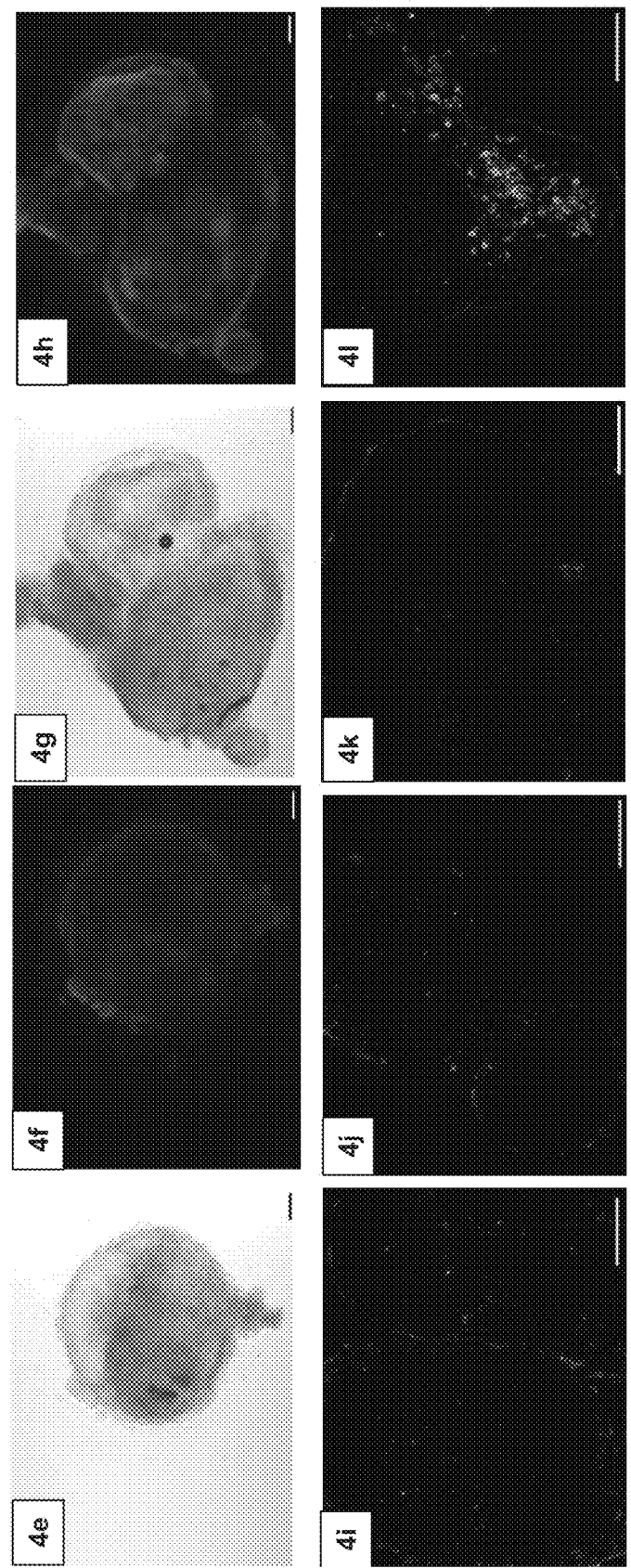
Figs. 4e-l

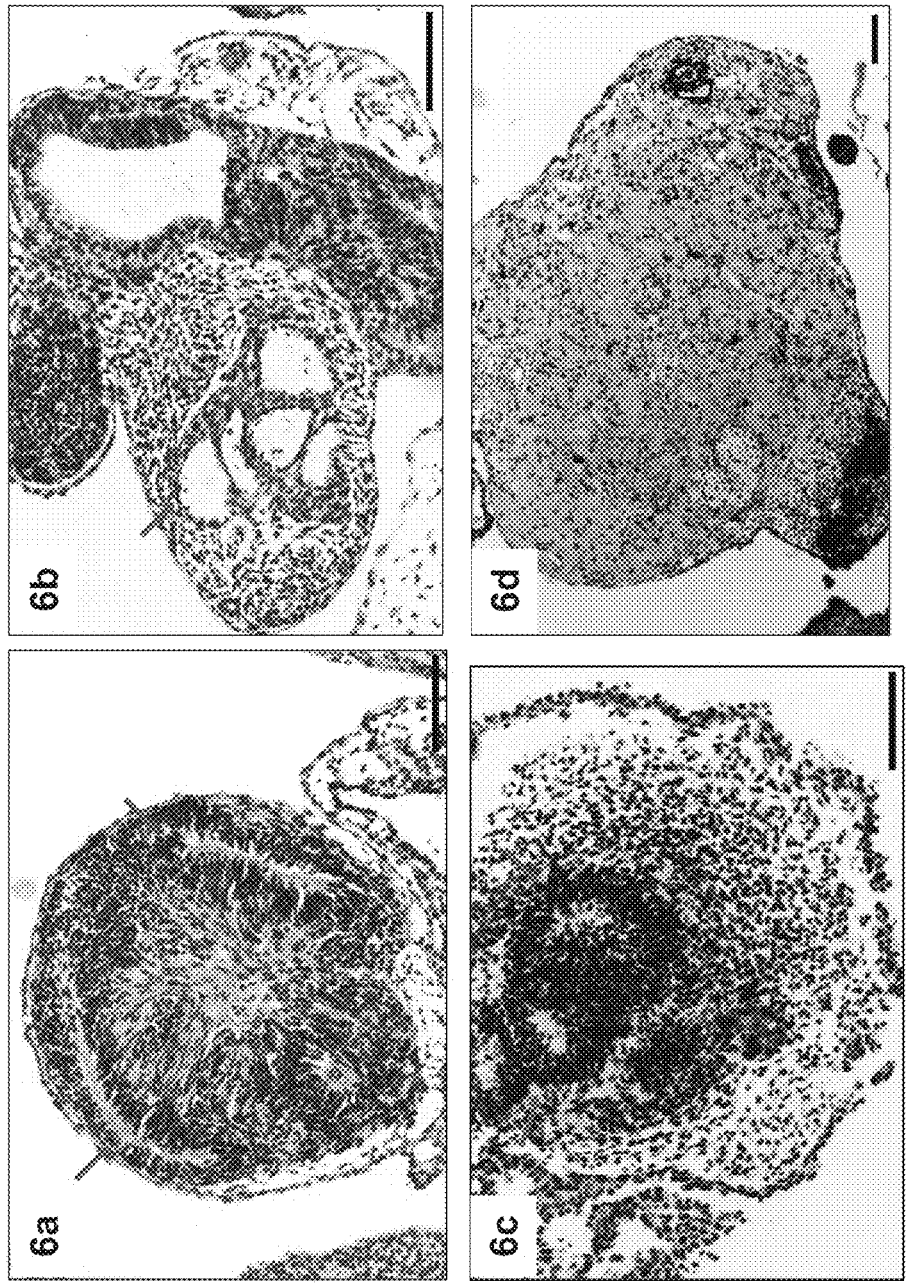
Figs. 6a-f

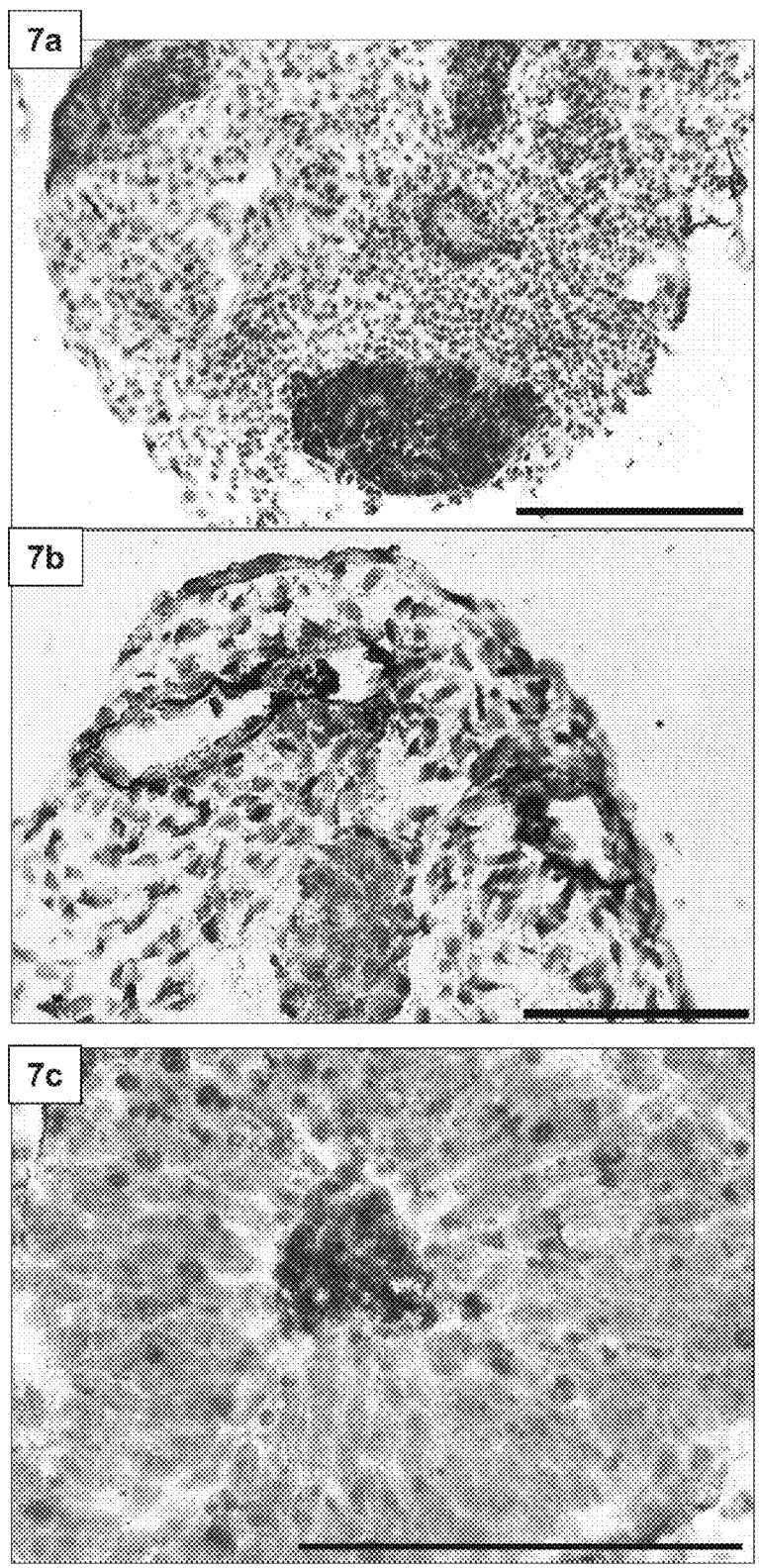
Figs. 7a-c

SEQUENCE LISTING

```
<160> NUMBER OF SEQ ID NOS: 22

<210> SEQ ID NO 1
<211> LENGTH: 22
<212> TYPE: DNA
<213> ORGANISM: Artificial sequence
<220> FEATURE:
```

<223> OTHER INFORMATION: Single strand DNA oligonucleotide

<400> SEQUENCE: 1
gagtgaaatg gcacgatacc ta                                    22

<210> SEQ ID NO 2
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 2
tttcctctcc ttcttcacct tc                                    22

<210> SEQ ID NO 3
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 3
gctgacctgg agatgcaaat tgagagcc                              28

<210> SEQ ID NO 4
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 4
gggcagcatt catttccaca ttcacatcac                            30

<210> SEQ ID NO 5
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 5
ggagttatgg tgggtatggg tc                                    22

<210> SEQ ID NO 6
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 6
agtggtgaca aaggagtagc ca                                    22

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
atgactgtga gcaggtgtgc                                       20

<210> SEQ ID NO 8

```
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 8
gtccagcgta tccacgatct                                                    20

<210> SEQ ID NO 9
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 9
tgcttgaatg tgctgatgac aggg                                               24

<210> SEQ ID NO 10
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 10
aaggcaagtc agcagccatc tcat                                               24

<210> SEQ ID NO 11
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 11
gctggattgt ctgcaggatg gggaa                                              25

<210> SEQ ID NO 12
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 12
tcccctgaag aaaattggtt aaaat                                              25

<210> SEQ ID NO 13
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 13
agacatcgca ctgactgaga ac                                                 22

<210> SEQ ID NO 14
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 14
```

```
gacgggtcac tatctgtgca ac                                              22
```

<210> SEQ ID NO 15
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 15

```
gagaacaatg agaaccttca ggaga                                           25
```

<210> SEQ ID NO 16
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 16

```
ttctggcgcc ggttacagaa cca                                             23
```

<210> SEQ ID NO 17
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 17

```
gtgtctgtgg ggtcatcc                                                   18
```

<210> SEQ ID NO 18
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 18

```
atcaaacagc ctcttcttgg c                                               21
```

<210> SEQ ID NO 19
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 19

```
caacgagaaa atgtcaga                                                   18
```

<210> SEQ ID NO 20
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 20

```
ggagccttcc gttctagagt                                                 20
```

<210> SEQ ID NO 21
<211> LENGTH: 20
<212> TYPE: DNA
<213> ORGANISM: Artificial sequence
<220> FEATURE:

-continued

```
<223> OTHER INFORMATION: Single strand DNA oligonucleotide

<400> SEQUENCE: 21
agccacatcg ctcagacacc                                              20

<210> SEQ ID NO 22
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 22
gtactcagcg ccagcatcg                                               19
```

METHOD OF DYNAMICALLY CULTURING EMBRYONIC STEM CELLS

RELATED PATENT APPLICATION

This application is a National Phase Application of PCT/IL03/01017 having International Filing Date of 30 Nov. 2003, which claims the benefit of U.S. Provisional Patent Application No. 60/429,574 filed 29 Nov. 2002.

FIELD AND BACKGROUND OF THE INVENTION

The present invention relates to a method of dynamically culturing human embryonic stem cells (hESCs) which method can be utilized for large scale production of embryoid bodies (EBs) and EBs-derived-cells and cell lines and thus is particularly suitable for the generation of cell cultures utilized in cell replacement therapy.

Human embryonic stem cells (hESCs) are proliferative, undifferentiated stem cells capable of being maintained in an undifferentiated state while preserving their pluripotent capacity.

ESCs can differentiate into cell types having a particular, specialized function (i.e., "fully differentiated" cells) or to cells capable of being maintained in an undifferentiated state (i.e., "pluripotent stem cells"). Upon removal from their cultures, ESCs can spontaneously differentiate into three-dimensional cell aggregates, which, overtime, increase in cell number and complexity and form embryoid bodies (EBs) (Thomson et al., 1998). EBs are morphological structures comprised of a population of ESCs and/or embryonic germ cells (EGCs) which have undergone differentiation. EBs formation initiates following the removal of differentiation blocking factors from ES cell cultures. In the first step of EBs formation, ESCs proliferate into small masses of cells which then proceed with differentiation. In the first phase of differentiation, following 1-4 days in culture for human ESCs, a layer of endodermal cells is formed on the outer layer of the small mass, resulting in "simple EBs". In the second phase, following 3-20 days post-differentiation, "complex EBs" are formed. Complex EBs are characterized by extensive differentiation of ectodermal and mesodermal cells and derivative tissues.

Stem-cell-derived-differentiated cells of specific lineages are of increasing importance for various therapeutic and tissue engineering applications. However, for both tissue regeneration and cell-replacement applications there is a need to develop methods of efficiently producing large quantities of EBs-derived-differentiated cells.

Prior art methods of generating EBs involve the initial aggregation of ESCs into spheroid, three-dimensional structures. Thus, when undifferentiated ESCs are removed from their feeder layers and transferred to liquid media using non-adherent tissue culture plates large aggregates of EBs are formed (Itskovitz-Eldor et al., 2000). However, the extent of EB aggregation should be carefully monitored and controlled since large agglomerated EBs are often accompanied with extensive cell death and necrosis due to mass transport limitations (Dang et al., 2002).

To overcome these limitations, methods of controlled agglomeration of EBs have been developed. These include the hanging drop method in which the ESCs are aggregated in hanging drops for two days prior to their transfer to liquid cultures. Another method utilizes semi-solid methylcellulose cultures in order to control EB's agglomeration (as disclosed by Dang et al., 2002 and in U.S. Pat. Appl. No. 20030119107). However, although adequate for small-scale laboratory purposes these systems are not amenable to large-scale clinical production due to the inability to control the extracellular components, which may affect EB's purity and reproducibility, as well as the cell types which can be readily generated therefrom [Maltepe, E. et al., (1997). Abnormal angiogenesis and responses to glucose and oxygen deprivation in mice lacking the protein ARNT. Nature, 386: 403-7; Soria, B. (2001). In vitro differentiation of pancreatic beta-cells. Differentiation 68: 205-19; Zandstra, P. W. and Nagy, A. (2001). Stem cell bioengineering. Annu Rev Biomed Eng 3:275-305]. On the other hand, prior art attempts to culture EBs in spinner flasks, as a simple, large-scale process, resulted in either the formation of large cell-clumps within a few days (Wartenberg et al., 2001), or in a massive hydrodynamic damage to the cells when extensive mixing was used (Chisti, 2001).

There is thus a widely recognized need for, and it would be highly advantageous to have, a method of dynamically generating hEBs devoid of the above described limitations.

SUMMARY OF THE INVENTION

According to one aspect of the present invention there is provided a method of dynamically generating embryoid bodies comprising culturing embryonic stem cells in a bioreactor selected capable of subjecting cells cultured in a fluid contained therein to randomized gravity vectors without formation of gas bubbles in the fluid to thereby obtain dynamically generated embryoid bodies.

According to another aspect of the present invention there is provided a cell culture comprising embryoid bodies, wherein at least 90% of the embryoid bodies fall within a diameter size range of 400-800 µm.

According to yet another aspect of the present invention there is provided a method of generating expanded and/or differentiated cells from embryonic stem cells comprising: (a) culturing embryonic stem cells in a bioreactor selected capable of subjecting cells cultured in a fluid contained therein to randomized gravity vectors without formation of gas bubbles in the fluid to thereby obtain dynamically generated embryoid bodies; (b) isolating lineage specific cells from the embryoid bodies, and; (c) culturing the lineage specific cells under culturing conditions selected suitable for the expansion and/or differentiation of the lineage specific cells to thereby obtain expanded and/or differentiated lineage-specific cells.

According to still another aspect of the present invention there is provided a method of treating a disorder requiring cell replacement therapy comprising: (a) culturing embryonic stem cells in a bioreactor selected capable of subjecting cells cultured in a fluid contained therein to randomized gravity vectors without formation of gas bubbles in the fluid to thereby obtain dynamically generated embryoid bodies; (b) isolating lineage specific cells from the embryoid bodies; (c) culturing the lineage specific cells under culturing conditions selected suitable for the expansion and/or differentiation of the lineage specific cells to thereby obtain expanded and/or differentiated lineage-specific cells, and; (d) administering cells of the expanded and/or differentiated lineage-specific cells to an individual in need thereof thereby treating the disorder requiring cell replacement therapy.

According to an additional aspect of the present invention there is provided a method of dynamically expanding embryonic stem cells while maintaining the embryonic stem cells in an undifferentiated state, the method comprising culturing embryonic stem cells in a bioreactor selected capable of subjecting cells cultured in a fluid contained therein to randomized gravity vectors without formation of gas bubbles in the fluid to thereby obtain dynamically expanded undifferentiated embryonic stem cell cultures.

According to further features in preferred embodiments of the invention described below, the bioreactor is capable of exerting a microgravitational force on the cells cultured therein.

According to still further features in the described preferred embodiments the microgravitational force is selected from the range of 0.05-0.9 G.

According to still further features in the described preferred embodiments the microgravitational force is 0.1 G.

According to still further features in the described preferred embodiments the bioreactor is capable of maintaining the embryonic stem cells in a state of free fall.

According to still further features in the described preferred embodiments the bioreactor is a tubular vessel having at least one vessel port for transferring materials into and out of the tubular vessel.

According to still further features in the described preferred embodiments the tubular vessel is rotating around a horizontal longitudinal axis.

According to still further features in the described preferred embodiments the bioreactor is capable of holding a fluid volume selected from the range of 1-500 ml.

According to still further features in the described preferred embodiments the bioreactor is capable of holding a fluid volume of 55 ml.

According to still further features in the described preferred embodiments a diameter of the tubular vessel is selected from range of 2.54-15.24 centimeters.

According to still further features in the described preferred embodiments culturing of the embryonic stem cells is effected in the tubular vessel under a rotational speed selected from a range of 15-20 rpm.

According to still further features in the described preferred embodiments the bioreactor enables oxygenation of the fluid via controlled diffusion of dissolved gasses.

According to still further features in the described preferred embodiments the embryonic stem cells are cultured at an initial concentration of $0.5-0.7 \times 10^6$ cells per milliliter medium.

According to still further features in the described preferred embodiments the bioreactor is a slow turning lateral vessel.

According to still further features in the described preferred embodiments culturing of the embryonic stem cells is effected in a culture medium selected suitable for embryoid bodies formation.

According to still further features in the described preferred embodiments the culture medium includes 80% KO-DMEM, 20% serum, 0.5% Penicillin-Streptomycin, 1 mM L-glutamine, 0.1 mM β-mercaptoethanol and 1% non-essential amino acid stock.

According to still further features in the described preferred embodiments culturing is effected over a culturing period of 1-35 days.

According to still further features in the described preferred embodiments culturing is effected for 30 days.

According to still further features in the described preferred embodiments at least 85% of the embryoid bodies are devoid of necrotic centers.

According to still further features in the described preferred embodiments isolating lineage specific cells is effected by sorting of cells contained within the embryoid bodies via fluorescence activated cell sorter.

According to still further features in the described preferred embodiments isolating lineage specific cells is effected by a mechanical separation of cells, tissues and/or tissue-like structures contained within the embryoid bodies.

According to still further features in the described preferred embodiments isolating lineage specific cells is effected by subjecting the embryoid bodies to differentiation factors to thereby induce differentiation of the embryoid bodies into lineage specific differentiated cells.

According to still further features in the described preferred embodiments the embryonic stem cells are attached to a carrier.

According to still further features in the described preferred embodiments the carrier is coated with a matrix selected capable of supporting a growth of the embryonic stem cells.

According to still further features in the described preferred embodiments culturing of the embryonic stem cells is effected in a culture medium selected suitable for expanding embryoid stem cell cultures in the undifferentiated state.

The present invention successfully addresses the shortcomings of the presently known configurations by providing methods of dynamically generating human embryoid bodies which can be used for generating lineage specific cells and cell lines useful in, for example, cell replacement therapy.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

The patent or application file contains at least one drawing executed in color. Copies of this patent or patent application publication with color drawing(s) will be provided by the Office upon request and payment of the necessary fee.

In the drawings:

Figure 1A:
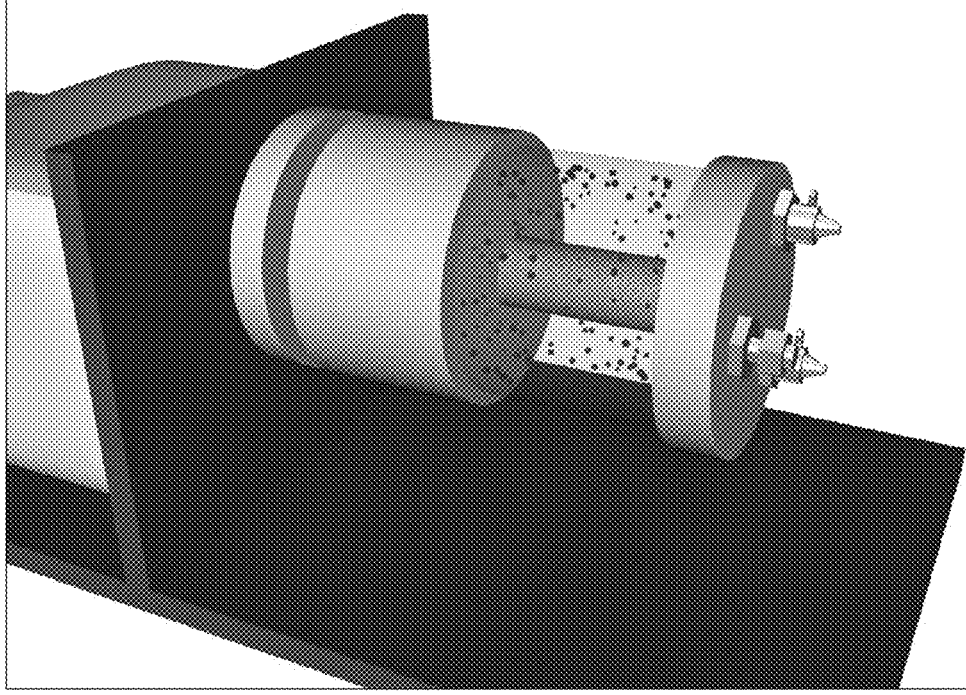
Figure 1B:
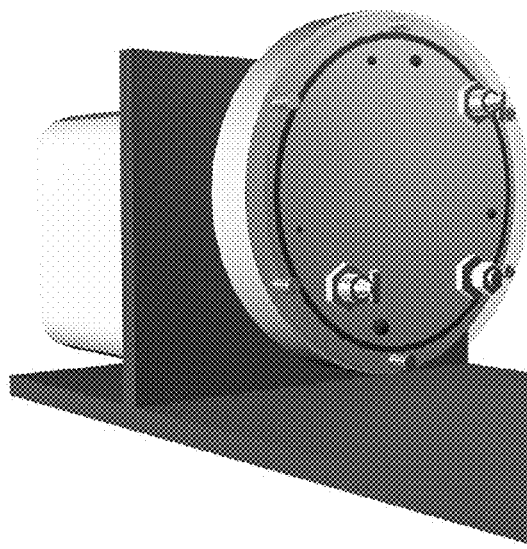

FIGS. 1*a-b* schematically illustrate the rotating bioreactors utilized by the present invention. FIG. 1*a*—the slow turning lateral vessel (STLV) system; FIG. 1*b*—the high aspect rotating vessel (HARV) system.

FIGS. 2*a-c* are photomicrographs of one-month-old EBs illustrating a dynamic formation using the various culturing systems. FIG. 2*a*—STLV; FIG. 2*b*—HARV; FIG. 2*c*—static petri dishes. Shown are Hematoxylin-Eosin (H&E) stained histological sections illustrating the formation of small and relatively homogenous population of hEBs generated in the STLV bioreactor (FIG. 2a), big cell clumps in EBs generated in the HARV bioreactor (FIG. 2b), and EB adherence events generated in the static culture (FIG. 2c, arrow). Size bar represents 100 μm.

FIGS. 3a-d illustrate the efficiency of hEBs formation in STLV versus static petri dish cultures. Shown are light photomicrographs of representative fields of hEBs generated using the STLV bioreactor (FIGS. 3a-b) or the static petri dish cultures (FIGS. 3c-d), one (FIGS. 3a, c) or two (FIGS. 3b, d) weeks following hESC seeding. Note the cyst formation and the EB adherence events (FIG. 3d, arrow and arrowhead, respectively) in hEBs generated in the static culture as compared with the multiple, small-size EBs generated in the STLV bioreactor. Size bar represents 100 μm.

Figure 3E:
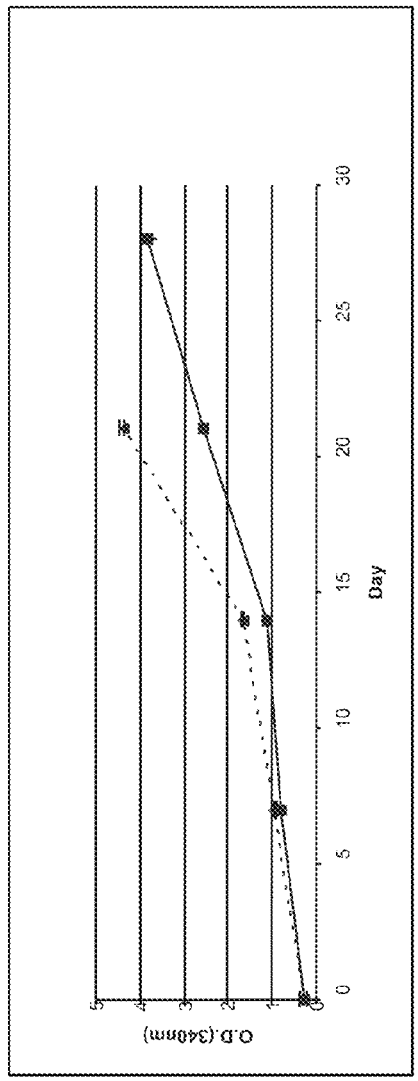
Figure 3F:
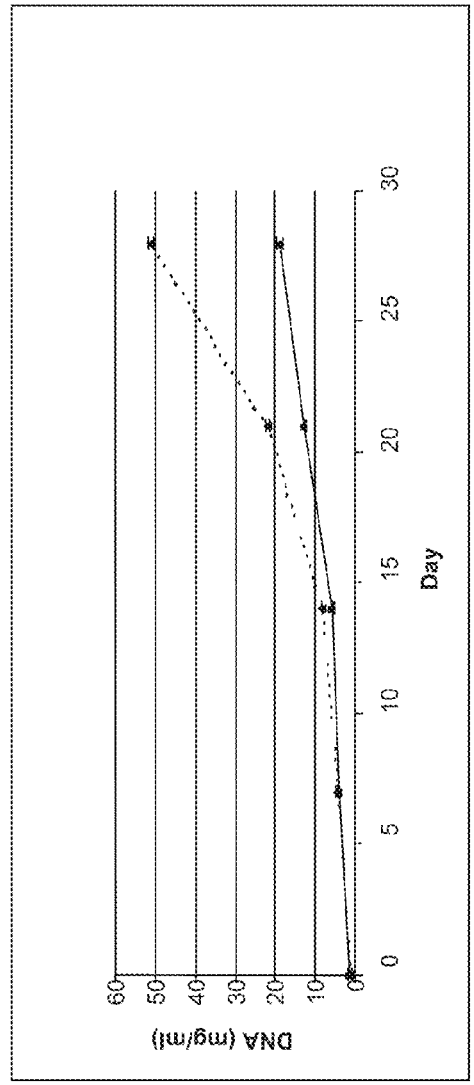
Figure 3G:
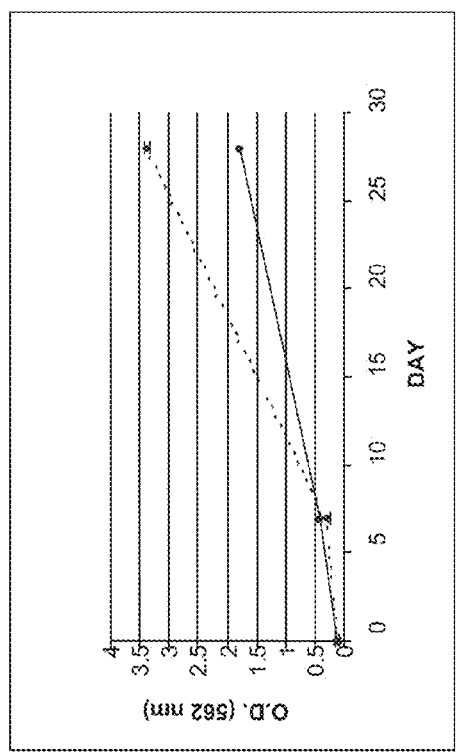
Figure 3H:
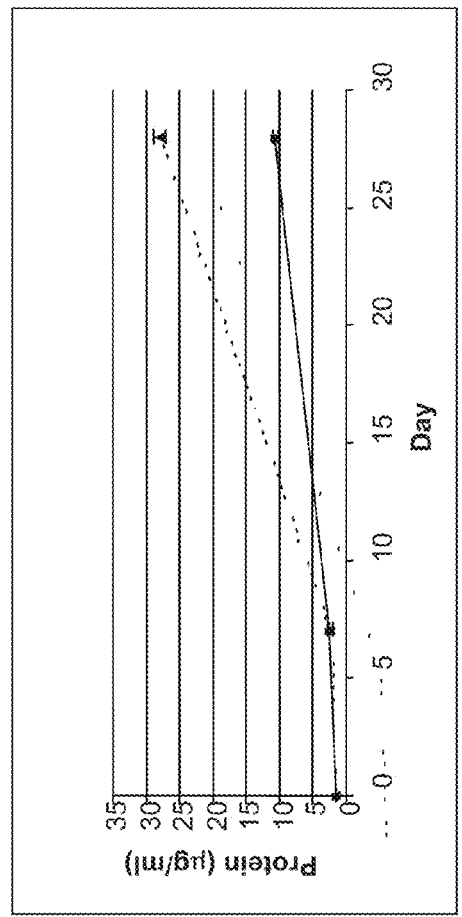

FIGS. 3e-h are time-course analyses comparing DNA and protein concentrations in EBs generated using the STLV bioreactor or the static petri dish cultures. FIG. 3e—raw data of Hoechst absorbance; FIG. 3f—calculated DNA concentration; FIG. 3g—raw data of 562 nm absorbance; FIG. 3h—calculated protein concentration; dashed line=STLV, solid line=static petri dishes.

Figure 4A:
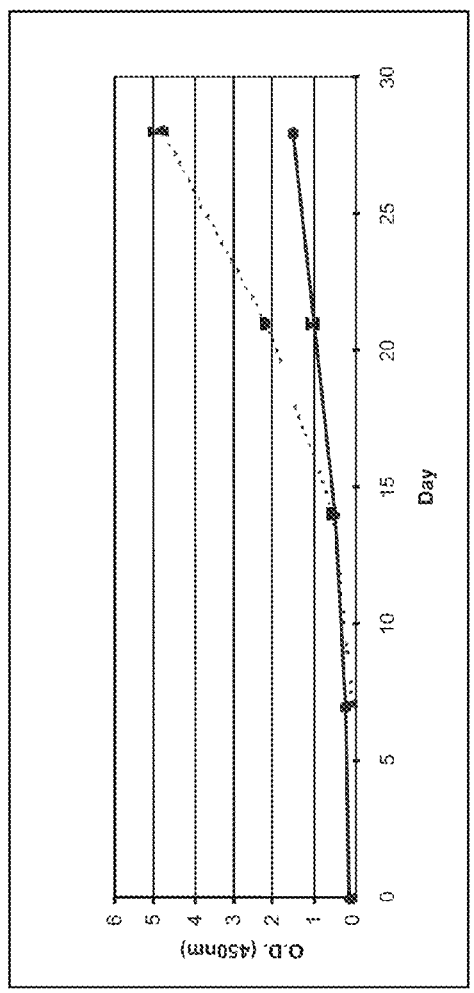
Figure 4B:
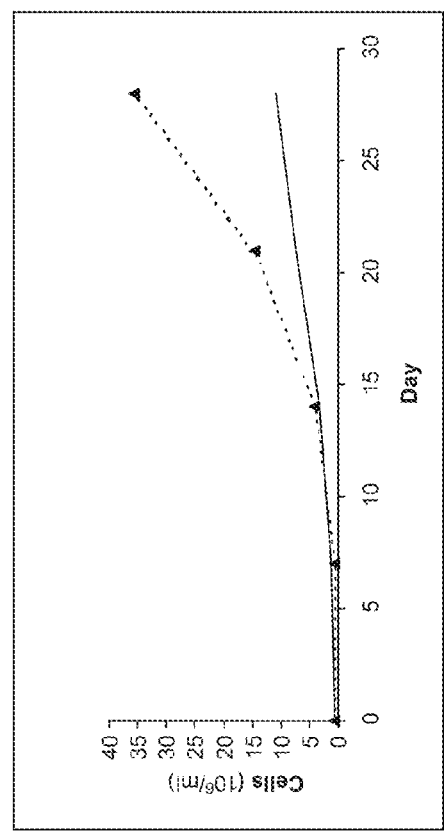
Figure 4C:
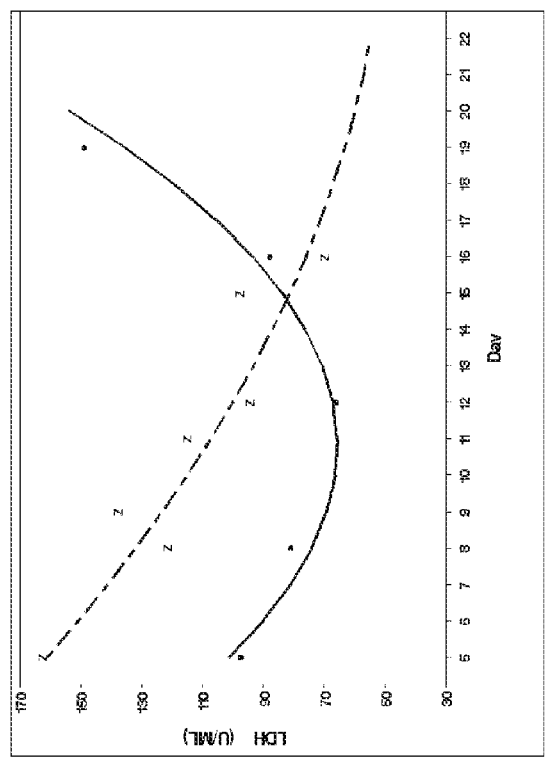
Figure 4D:
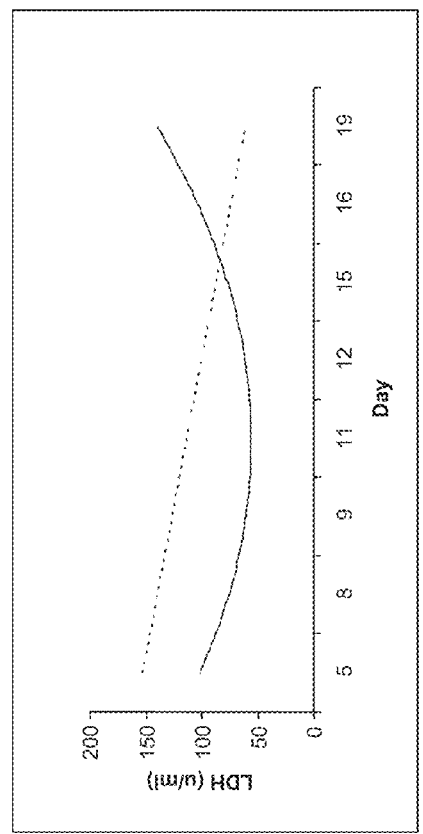

FIGS. 4a-l illustrate cell viability during hEBs formation and cultivation in STLV and static cultures. FIGS. 4a-d are time-course analyses comparing the viable cells (XTT) and lactate dehydrogenase (LDH) activity in EBs generated using the STLV bioreactor or the static petri dish cultures. FIG. 4a—raw data of XTT; FIG. 4b—calculated XTT; FIG. 4c—raw data LDH; FIG. 4d—LDH leakage; dashed line=STLV, solid line=static petri dishes. FIGS. 4e-h are photomicrographs depicting cell viability using Ethidium homodimer-1 (EthD-1) staining in hEBs generated using STLV (FIGS. 4e-f) or static (FIGS. 4g-h) cultures. FIG. 4e—light photomicrograph; FIG. 4f—fluorescence photomicrograph; FIG. 4g—light photomicrograph; FIG. 4h—fluorescence photomicrograph. Note the faint red staining observed in EBs generated using the STLV bioreactor (FIG. 4f) as compared with the strong red staining observed in EBs generated using static cultures (FIG. 4h). FIGS. 4i-l are fluorescence photomicrographs of representative EBs depicting DNA strand breaks following a tunnel assay. FIGS. 4i-j—EBs generated using the STLV bioreactor; FIGS. 4k-l—EBs generated using the static cultures. Note the presence of significant green fluorescence in EBs generated using the static cultures as compared with the nearly absence of green fluorescence in EBs generated using the STLV bioreactor.

Figure 5A:
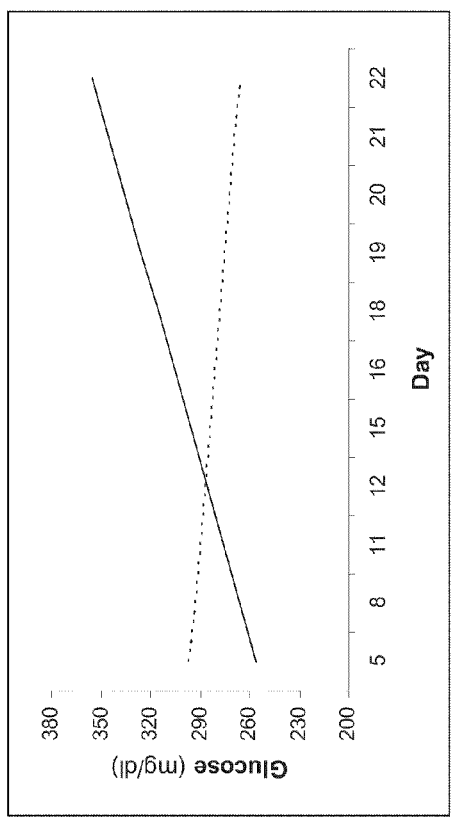
Figure 5B:
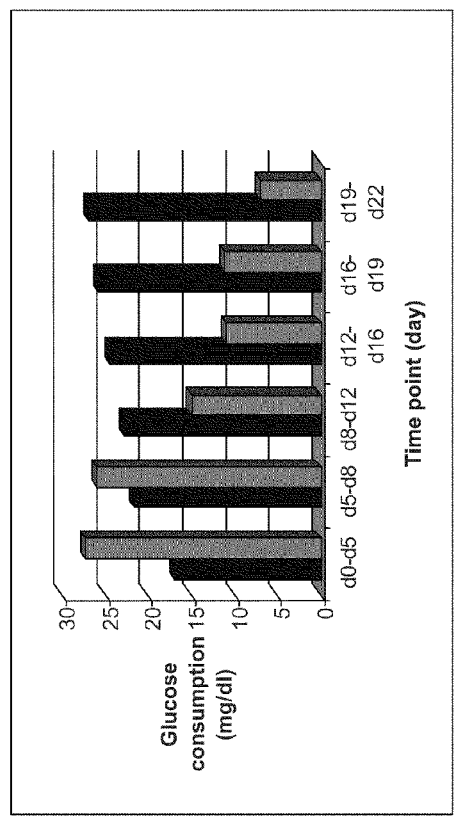
Figure 5C:
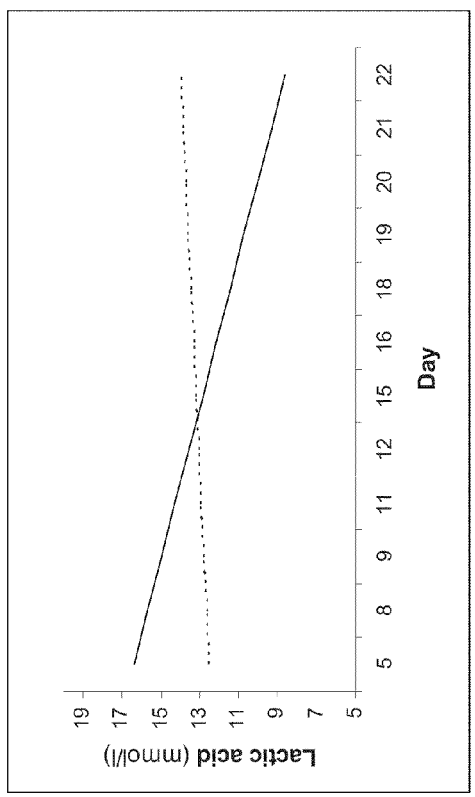
Figure 5D:
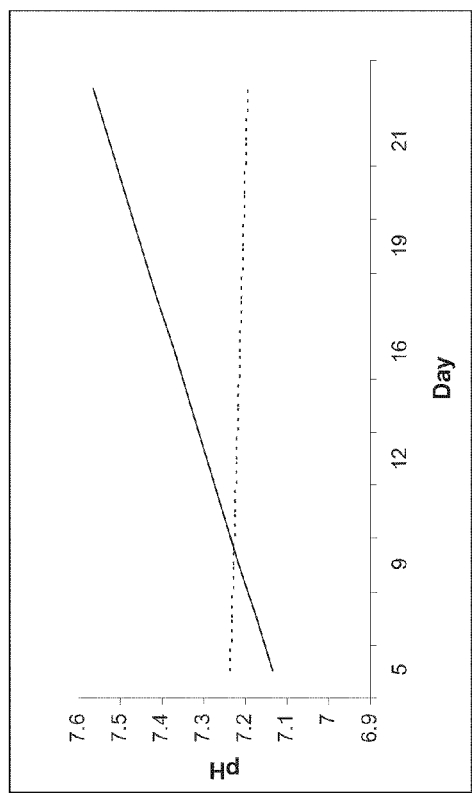
Figure 5E:
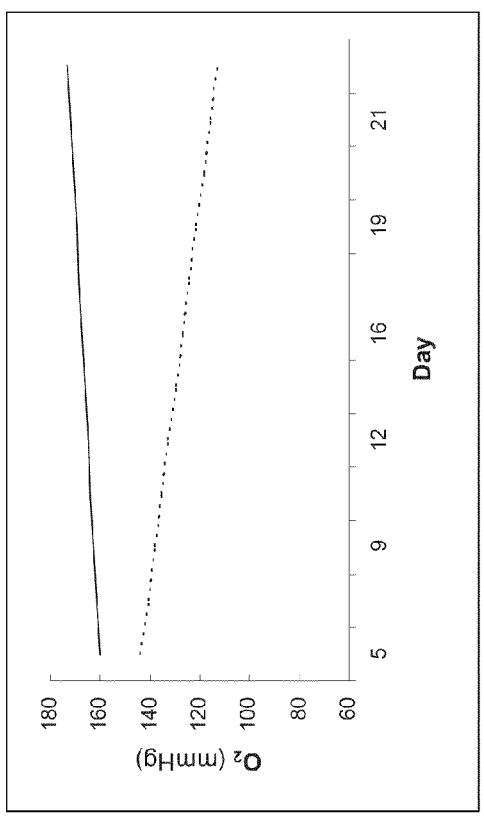
Figure 5F:
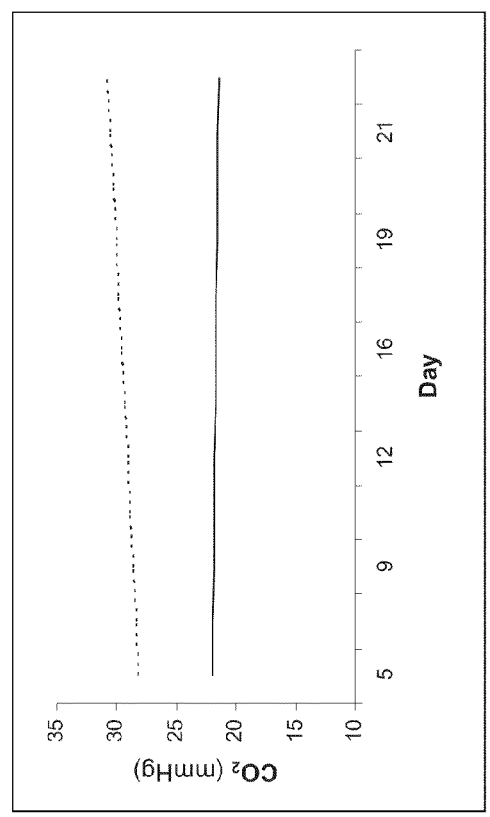

FIGS. 5a-f are graphs illustrating medium metabolic indices in STLV and static cultures along the culture period. FIG. 5a—measured glucose level in medium; FIG. 5b—calculated glucose consumption rate; FIG. 5c—lactic acid production; FIG. 5d—pH; FIG. 5e—$pO_2$; FIG. 5f—$pCO_2$; Data represent the average of 3 independent experiments; Dashed lines or black columns=STLV bioreactor, solid lines and gray columns=static cultures. Note the enhanced metabolism detected in the STLV system using the glucose consumption, lactic acid production and pH indices.

Figure 6F:
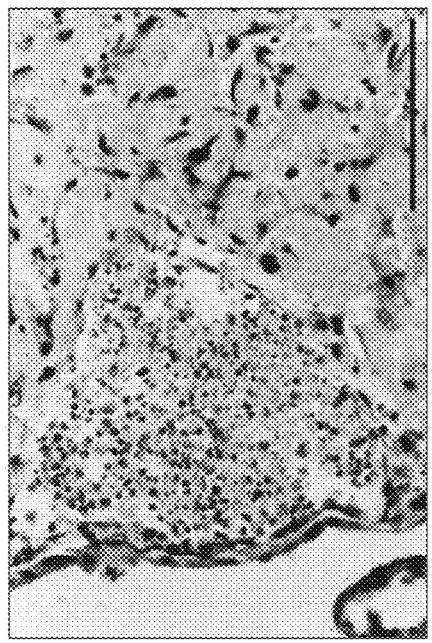

FIGS. 6a-f are photomicrographs illustrating the differentiation stage of EBs generated using the STLV (FIG. 6a-c) or the HARV (FIG. 6d-f) bioreactors. Shown are H&E stained histological sections of one-month-old EBs. Note that while the STLV-generated EBs differentiated into epithelial neuronal tubes (FIG. 6a, arrows), blood vessels (FIG. 6b, arrows) and glands (FIG. 6c, arrows) the HARV-generated EBs included a large necrotic area (FIG. 6d) as well as some indication of differentiation mainly observed at the edges of the cell clumps, such as primitive blood cells (FIG. 6e) and cartilage-like structures (FIG. 6f). Size bar represents 100 μm.

FIGS. 7a-c are immunohistochemistry analyses depicting the expression of differentiation markers in one-month-old hEBs generated using the STLV bioreactor. Shown are light photomicrographs of hEBs labeled with anti glial fibrillary acidic protein (GFAP, FIG. 7a), anti CD34 (FIG. 7b) and anti somatostatin (FIG. 7c) antibodies. Note the positive staining of the primitive neuronal tubes with GFAP staining, the blood vessels with CD34 staining and the well-organized pillari epithelial tubes with somatostatin staining. Size bar represents 100 μm.

Figure 7D:
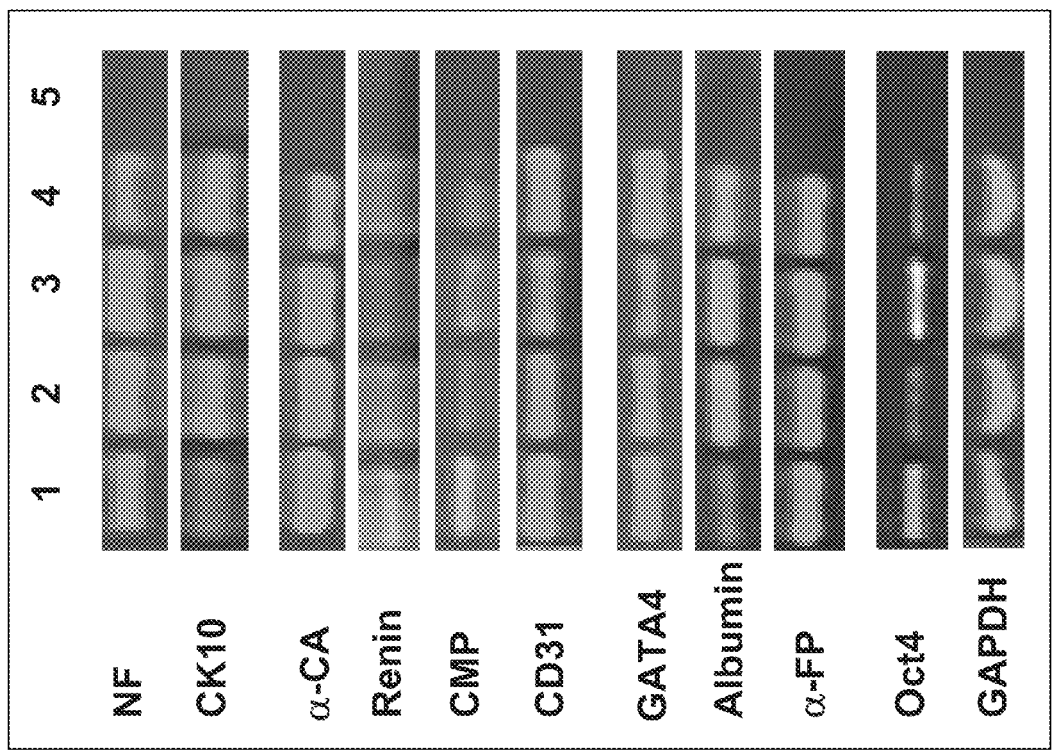

FIG. 7d illustrates RT-PCR determination of the expression of various genes representing all three embryonic germ layers in hEBs. NF=Neurofilament 68 KD (GenBank Accession No: AY156690); CK10=Cytokeratin 10 (GenBank Accession No: XM_352919); αCA=α-cardiac actin (GenBank Accession No: NM_005159); Renin (GenBank Accession No: AY436324); CMP=cartilage matrix protein (GenBank Accession No: NM_002379); CD31 (GenBank Accession No: NM_000442); GATA4 (GenBank Accession No: NM_002052); Albumin (GenBank Accession No: AF542069); αFP=α-fetoprotein (GenBank Accession No: BC027881); Oct4 (GenBank Accession No: S81255); GAPDH=glyceraldehyde-3-phosphate dehydrogenase (GenBank Accession No:J04038). Lane 1-7-day-old hEBs generated using the STLV culture; lane 2-30-day-old hEBs generated using the STLV culture; lane 3-7-day-old hEBs generated using the static culture; lane 4-30-day-old hEBs generated using the static culture; The specificity of the reaction was verified in the absence of RNA (FIG. 7d, lane 5).

DESCRIPTION OF THE PREFERRED EMBODIMENTS

The present invention is of a method of dynamically generating human embryoid bodies which can be used for generating lineage specific cells and cell lines useful in, for example, cell replacement therapy.

The principles and operation of the method of dynamically generating human embryoid bodies according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Human embryonic stem cells (hESCs) are of increasing importance as a potential source of all types of differentiated cells useful in various therapeutic and tissue engineering applications.

Although there are numerous approaches for generating stem cell-derived-differentiated cells, approaches which employ an embryoid body (EB) forming step are presently preferred since they imitate embryogenesis.

EBs are formed following the removal of ESCs from feeder layer-, or matrix-based cultures into suspension cultures. The first and most critical step in the development of EB is the formation of ESC aggregates. The extent of aggregation should be carefully monitored and controlled since large agglomerated EBs are often characterized by extensive cell death and necrosis due to mass transport limitations (Dang et al., 2002).

Previous attempts to generate EBs utilized the hanging drops (Kuo, H. C. et al., 2003. Differentiation of monkey embryonic stem cells into neural lineages. Biol Reprod. 68: 1727-35) or the semi-solid methylcellulose culture approaches (Dang et al., 2002; U.S. Pat. Appl. No. 20030119107 to Dang, S. et al). Although such culturing conditions might be suitable for research purposes, they are limited by variable and uncontrolled extracellular components.

Attempts to dynamically generate EBs in spinner flasks resulted in either the formation of large cell-clumps within a few days (Wartenberg et al., 2001), or in a massive hydrodynamic damage to the cells when extensive mixing was used (Chisti, 2001). Moreover, oxygenation and suspension of cells using prior art methods have subjected the ESCs to the destructive forces caused by gas bubbles.

While reducing the present invention to practice, the present inventors have devised a novel culturing approach which is particularly suitable for generating EBs under dynamic culturing conditions and thus can be used for large-scale production of lineage specific-differentiated cells. As is illustrated in Examples 1 and 2 of the Examples section which follows, EBs generated using such an approach were devoid of necrotic centers and consisted of a homogenous, small-size EB culture, i.e., at least 90% of the EBs exhibited a diameter size of 400-800 µm.

Thus, according to one aspect of the present invention there is provided a method of dynamically generating embryoid bodies.

The method is effected by culturing embryonic stem cells (ESCs) in a bioreactor capable of subjecting cells cultured in a fluid contained therein to randomized gravity vectors without formation of gas bubbles in the fluid.

Such conditions assure that cultured ESCs are subjected to a constant gentle movement, with increased cell-cell interactions, and yet are not exposed to destructive forces which can result from fluid flow and/or presence of gas bubbles.

As used herein, the term "randomized gravity vectors" refers to subjecting the cells to varying gravity vectors during culturing in order to prevent the dictation of a growth direction by a single gravity vector. Thus, cells and/or tissues cultured under randomized gravity vectors can grow in all directions.

To generate randomized gravity vectors the bioreactor used by the present invention is preferably a tubular shaped vessel capable of rotating around its central spin axis, preferably around a horizontal longitudinal axis.

Preferably, the diameter of the tubular shaped bioreactor used by the present invention is in the range of 2.54 to 15.24 cm., more preferably, in the range of 2.54 to 7.62 cm., most preferably the diameter of the tubular bioreactor is 2.54 cm.

To minimize the effect of a gravitational force on the cultured ESCs, the bioreactor is preferably capable of exerting a microgravitational force which enables the cells to freely interact with each other without being dictated by a gravitational force.

Preferably, the microgravitational force exerted by the bioreactor of the present invention is selected from the range of 0.05-0.9 G, more preferably 0.05-0.5 G, most preferably 0.1 G.

Thus, cells cultured in the bioreactor according to the teachings of the present invention are subjected to randomized microgravity vectors which in essence generate an environment in which the cells are in a state of constant "free fall". Under these conditions the fluid and the cells contained therein are mixed and suspended without being subjected to destructive or stressful forces, such as those present in other dynamic methods using stirrers, airlifts and/or agitators.

Moreover, by exposing the cells to random gravity forces, the cultured cells are capable of multi-directional growth and are therefore capable of efficiently aggregating into three-dimensional structures.

To optimize gas and oxygen supply to and from the ESC culture, the bioreactor further includes one or more vessel ports for transferring materials such as oxygen and other gasses into and out of the tubular vessel.

Preferably, the bioreactor is equipped with a membrane diffusion gas exchange system. Thus, oxygenation is effected by active or passive diffusion which results in the exclusion of all but dissolved gasses from the reactor chamber, yielding a vessel devoid of gas bubbles and gas/fluid interfaces.

Moreover, the bioreactor used by the present invention is preferably designed to enable efficient gas exchange by providing a high ratio between the membrane area and the volume of medium.

Suitable bioreactors for use along with the present invention, include, but are not limited to, the rotating cell culture systems (RCCS) developed by NASA, which are described in details in U.S. Pat. Nos. 5,763,279 and 5,437,998 to Schwartz et al., Examples of RCCS include the Slow Turning Lateral Vessel (STLV) and the High Aspect Ratio Vessel (HARV) which are further described in Example 1 of the Examples sections which follows. Briefly, the STLV bioreactor is a tubular shaped chamber with a central gas transfer cord, and the HARV bioreactor is a disc shaped culture chamber in which the oxygenator membrane forms the inside wall of the vessel.

Preferably, the bioreactor utilized by the present invention is the STLV. As is shown in Example 1 of the Examples section which follows, EBs generated following one month of culturing using the STLV bioreactor exhibited relatively homogenous small aggregates of viable cells.

As is mentioned hereinabove, the ESCs are cultured in a fluid contained within the bioreactor. Preferably, the bioreactor of the present invention is capable of holding a fluid volume in the range of 1-500 ml. more preferably, 10-250 ml. most preferably 20-150 ml.

According to presently preferred configurations, the bioreactor used by the present invention is capable of holding a fluid volume of 55 ml.

As used herein, the term "culturing" refers to seeding the ESCs along with their culture medium in the bioreactor of the present invention and subjecting the cells to the appropriate culturing temperatures (e.g., 37° C.), supply of oxygen and gasses and randomized microgravity vectors as described hereinabove.

It will be appreciated that the concentration of ESCs in the culture might affect the rate of cell aggregation and the size of the generated EBs, thus, according to specific embodiments of the present invention, ESCs are seeded in the bioreactor at a cell concentration range of 0.1 to $2.0 \times 10^6$ cells/ml., more preferably, 0.1 to $1.5 \times 10^6$ cells/ml., more preferably, 0.1 to $1.2 \times 10^6$ cells/ml., more preferably, 0.2 to $1.0 \times 10^6$ cells/ml., more preferably, 0.4 to $0.8 \times 10^6$ cells/ml., most preferably at 0.5 to $0.7 \times 10^6$ cells/ml.

ESCs of the present invention can be obtained from the embryonic tissue formed after gestation (e.g., blastocyst), or embryonic germ (EG) cells. Stem cell derivation and preparation is further described hereinbelow. Preferred stem cells of the present invention are human embryonic stem cells.

The ESCs of the present invention can be obtained using well-known cell-culturing methods. For example, human ESCs can be isolated from human blastocysts. Human blastocysts are typically obtained from human in vivo preimplantation embryos or from in vitro fertilized (IVF) embryos.

Alternatively, a single cell human embryo can be expanded to the blastocyst stage. For the isolation of human ESCs the zona pellucida is removed from the blastocyst and the inner cell mass (ICM) is isolated by immunosurgery, and the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ESCs are then routinely split every 1-2 weeks. For further details on methods of preparation human ESCs see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; Gardner et al., [Fertil. Steril. 69: 84, 1998].

It will be appreciated that commercially available stem cells can also be used by the dynamic culturing method of the present invention. Human ESCs can be purchased from the NIH human embryonic stem cells registry (http://escr.nih.gov). Non-limiting examples of commercially available embryonic stem cell lines are BG01, BG02, BG03, BG04, CY12, CY30, CY92, CY10, TE03 and TE32.

ESCs used by the present invention can be also derived from human embryonic germ cells (EGCs). Human EGCs are prepared from the primordial germ cells obtained from human fetuses of about 8-11 weeks of gestation using laboratory techniques well known to the skilled artisan. Briefly, genital ridges are dissociated and cut into small chunks which are thereafter disaggregated into cells by mechanical dissociation. EGCs are then grown in tissue culture flasks with the appropriate medium. The cells are cultured with daily replacement of medium until a cell morphology consistent with EGCs is observed, typically after 7-30 days or 1-4 passages. For additional details on methods of preparation human EGCs see Shamblott et al., [Proc. Natl. Acad. Sci. USA 95: 13726, 1998] and U.S. Pat. No. 6,090,622.

To prevent hydrodynamic damage to the ESCs cultured according to the teachings of the present invention, the rotation speed of the bioreactor should be carefully monitored.

According to preferred embodiments the bioreactor used by the present invention is set at a rotating speed selected from the range of 0.1-100 rpm, more preferably, 10-30 rpm, most preferably 15-20 rpm.

To enable differentiation of ESCs into EBs, the fluid contained within the bioreactor is preferably a tissue culture medium selected suitable for ESC differentiation.

Although RCCS vessels have been previously used for culturing neurons, bone and cartilage, heart cells, kidney cells and hepatocytes, in the presence of various growth factors and hormones which dictate differentiation towards specific cell types, the culturing conditions used for generating EBs are preferably devoid of such restricting growth factors.

The culture medium used by the present invention to induce ESCs differentiation is preferably knockout KO-DMEM medium which is a water based medium that includes salts and essential proteins and is available from Gibco-Invitrogen Corporation products, Grand Island, N.Y., USA.

Preferably, the culture medium includes serum or serum replacement. According to specific embodiments, the serum of the present invention is provided at a concentration of at least 5%, more preferably, at least 15% and most preferably at a concentration of 20%.

To reduce intracellular oxidative reactions, β-mercaptoethanol, an anti-oxidant agent, is preferably added to the culture medium.

In addition, to avoid bacterial contamination during culturing, low concentration of Penicillin and Streptomycin are added to the culture medium.

Thus, according to presently preferred configurations the culture medium of the present invention includes 80% KO-DMEM, 20% serum, 0.5% Penicillin-Streptomycin, 1 mM L-glutamine, 0.1 mM β-mercaptoethanol and 1% non-essential amino acid stock, all of which are available from Gibco-Invitrogen Co.

It will be appreciated that the formation of embryo-like structures including all three embryonal germ layers from ESC aggregates is a time-dependent process which depends upon the ability of ESCs to co-localize, communicate with each other and form three-dimensional structures while differentiating into EBs.

According to specific embodiments of the present invention the culturing period needed for generating EBs varies from 1-35 days, depending on the stage of the EB required (e.g., simple or complex EB). In addition, the culturing period can vary depending on the culture medium and rotation speed used by the bioreactor.

According to presently preferred configurations, culturing is effected for 30 days in the STLV bioreactor which holds 55 ml. of culture medium and rotates at a rotational speed of 15-20 rpm.

It will be appreciated that EBs can be collected at any time during culturing and examined using an inverted light microscope. Thus, EBs can be assessed for their size and shape at any point in the culturing period. Examples of various EBs structures are shown in FIGS. 2a-c and 3a-d in the Examples section which follows.

During the culturing step, EBs can be monitored for their viability using methods known in the arts, including, but not limited to, DNA (Brunk, C. F. et al., Analytical Biochemistry 1979, 92: 497-500) and protein (e.g., using the BCA Protein Assay kit, Pierce, Technology Corporation, New York, N.Y., USA) contents, medium metabolite indices, e.g., glucose consumption, lactic acid production, LDH (Cook J. A., and Mitchell J. B. Analytical Biochemistry 1989, 179: 1-7) and medium acidity, as well as by using the XTT method of detecting viable cells [Roehm, N. et al., An improved colorimetric assay for cell proliferation and viability utilizing the tetrazolium salt XTT J. Immunol. Meth. 142, 257-265 (1991); Scudiero, D. et al., Evaluation of a soluble tetrazolium/formazan assay for cell growth and drug sensitivity in culture using human and other cell lines. Cancer Res. 48, 4827-4833 (1988); Weislow, O. et al., New soluble-formazan assay for HIV-1 cytopathic effects: Application to high-flux screening of synthetic and natural products for AIDS-antiviral activity. J. Natl. Cancer Inst. 81, 577-586 (1989)].

As is illustrated in Example 2 of the Example section which follows, EBs generated according to the method of the present invention and using the STLV bioreactor, exhibited increased glucose consumption and lactic acid production along with increased culture acidity, all of which are indicative of increased proliferation and EB development.

It will be appreciated that viability of cells in culture can also be assessed using various staining methods known in the art. For example, unfixed cells can be stained with the fluorescent dye Ethidium homodimer-1 (excitation, 495 nm; emission, 635 nm) which is detectable in cells with compromised membranes, i.e., dead cells. In this assay, live cells have a green fluorescent cytoplasm but no EthD-1 signal, whereas dead cells lack the green fluorescence and are stained with EthD-1. In addition, the Tunnel assay can be used to label DNA breaks which are characteristics of cells going through apoptosis. Another suitable assay is the live/dead viability/cytotoxicity two-color fluorescence assay, available from Molecular Probes (L-3224, Molecular Probes, Inc., Eugene, Oreg., USA). This assay measures intracellular esterase activity with a cell-permeable substrate (Calcein-AM) which is converted by live cells to a fluorescent derivative (polyanion calcein, excitation, 495 nm; emission, 515 nm) which is thereafter retained by the intact plasma membrane of live cells.

As is further shown in Example 2 of the Examples section which follows, EBs generated using the present methodology exhibited less staining than EBs generated using static cultures when either the Ethidium homodimer-1 dye or the Tunnel assay were employed. Altogether, these results demonstrate that the method of the present invention is more efficient in generating viable, proliferative EBs than the prior art methods.

During the culturing period, EBs are further monitored for their differentiation state. Cell differentiation can be determined upon examination of cell or tissue-specific markers which are known to be indicative of differentiation. For example, EB-derived-differentiated cells may express the neurofilament 68 KD which is a characteristic marker of the ectoderm cell lineage.

The differentiation level of the EBs can be monitored by following the loss of expression of the embryonic transcription factor Oct-4, and the increased expression level of other markers such as α-fetoprotein, NF-68 kDa, α-cardiac and albumin. Methods of determining the level of gene expression are known in the arts and include, but are not limited to RT-PCR, semi-quantitative RT-PCR, Northern blot, RNA-in situ hybridization and in situ RT-PCR.

As is shown in Examples 3 of the Examples section which follows, EBs cultured using the present approach expressed neurofilament 68 KD (NF) and cytokeratin 10 (CK10) which represent the ectoderm layer, α-cardiac actin (α-CA), renin, cartilage matrix protein (CMP) and CD31, which represent the mesoderm and albumin, ectoderm α-fetoprotein, and transcription factor GATA4 which represent the endoderm. Moreover, as is further shown in Example 3 of the Examples section which follows, the expression of Oct-4 decreased from 7-day-old EBs to 30-day-old EBs, demonstrating the decrease in undifferentiated ESCs along with EB formation.

In addition, tissue/cell specific markers can be detected using immunological techniques well known in the art [Thomson J A et al., (1998). Science 282: 1145-7]. Examples include, but are not limited to, flow cytometry for membrane-bound markers, immunohistochemistry for extracellular and intracellular markers and enzymatic immunoassay, for secreted molecular markers.

As is further shown in Examples 1 and 2 of the Example section which follows, when ESCs are cultured according to the method of the present invention and using the STLV bioreactor, multiple small-size EBs are obtained.

Thus, according to another aspect of the present invention, there is provided a cell culture comprising EBs, wherein at least 90% of the EBs fall within a diameter size range of 400-800 μm.

It will be appreciated that small-size EBs are more advantages than large-size EBs since they readily enable mass transport such as oxygen to and from the cells forming the EBs, thus preventing cell death and necrosis typical of large sized EBs.

Indeed, as is further illustrated in Examples 1 and 2 of the Examples section which follows, while EBs generated using the prior art methods (e.g., the static cultures) included cell clumps and necrotic centers in at least 40% of the EBs, at least 85% of EBs generated using the teachings of the present invention were devoid of necrotic centers.

Altogether, the results presented in Examples 1-3 of the Examples section which follows demonstrate that the method of the present invention enables generation of a homogeneous population of small-size, viable EBs which are devoid of necrotic centers. The EBs of the present invention are therefore highly amendable for large-scale production of EBs-derived-lineage specific cells.

Thus, according to another aspect of the present invention there is provided a method of generating expanded and/or differentiated cells from embryonic stem cells.

The method comprising isolating lineage specific cells from the EBs of the present invention and culturing the lineage specific cells under culturing conditions selected suitable for the expansion and/or differentiation of the lineage specific cells to thereby obtain expanded and/or differentiated lineage-specific cells.

As used herein, the phrase "isolating lineage specific cells" refers to the enrichment of a mixed population of cells in a culture with cells predominantly displaying at least one characteristic associated with a specific lineage phenotype. It will be appreciated that all cell lineages are derived from the three embryonic germ layers. Thus, for example, hepatocytes and pancreatic cells are derived from the embryonic endoderm, osseous, cartilaginous, elastic, fibrous connective tissues, myocytes, myocardial cells, bone marrow cells, vascular cells (namely endothelial and smooth muscle cells), and hematopoietic cells are differentiated from embryonic mesoderm and neural, retina and epidermal cells are derived from the embryonic ectoderm.

According to preferred embodiments of the present invention, isolating is effected by sorting of cells of the EBs via fluorescence activated cell sorter (FACS).

Methods of isolating EB-derived-differentiated cells via FACS analysis are known in the art. According to one method, EBs are disaggregated using a solution of Trypsin and EDTA (0.025% and 0.01%, respectively), washed with 5% fetal bovine serum (FBS) in phosphate buffered saline (PBS) and incubated for 30 min on ice with fluorescently-labeled antibodies directed against cell surface antigens characteristics to a specific cell lineage. For example, endothelial cells are isolated by attaching an antibody directed against the platelet endothelial cell adhesion molecule-1 (PECAM1) such as the fluorescently-labeled PECAM1 antibodies (30884X) available from PharMingen (PharMingen, Becton Dickinson Bio Sciences, San Jose, Calif., USA) as described in Levenberg, S. et al., (Endothelial cells derived from human embryonic stem cells. Proc. Natl. Acad. Sci. USA. 2002. 99: 4391-4396). Hematopoietic cells are isolated using fluorescently-labeled antibodies such as CD34-FITC, CD45-PE, CD31-PE, CD38-PE, CD90-FITC, CD117-PE, CD15-FITC, class I-FITC, all of which IgG1 are available from PharMingen, CD133/1-PE (IgG1) (available from Miltenyi Biotec, Auburn, Calif.), and glycophorin A-PE (IgG1), available from Immunotech (Miami, Fla.). Live cells (i.e., without fixation) are analyzed on a FACScan (Becton Dickinson Bio Sciences) by using propidium iodide to exclude dead cells with either the PC-LYSIS or the CELLQUEST software. It will be appreciated that isolated cells can be further enriched using magneticallylabeled second antibodies and magnetic separation columns (MACS, Miltenyi) as described by Kaufman, D. S. et al., (Hematopoietic colony-forming cells derived from human embryonic stem cells. Proc. Natl. Acad. Sci. USA. 2001, 98: 10716-10721).

According to yet an additional preferred embodiments of the present invention, isolating is effected by a mechanical separation of cells, tissues and/or tissue-like structures contained within the EBs.

For example, beating cardiomyocytes can be isolated from EBs as disclosed in U.S. Pat. Appl. No. 20030022367 to Xu et al., Four-day-old EBs of the present invention are transferred to gelatin-coated plates or chamber slides and are allowed to attach and differentiate. Spontaneously contracting cells, which are observed from day 8 of differentiation, are mechanically separated and collected into a 15-mL tube containing low-calcium medium or PBS. Cells are dissociated using Collagenase B digestion for 60-120 minutes at 37° C., depending on the Collagenase activity. Dissociated cells are then resuspended in a differentiation KB medium (85 mM KCl, 30 mM $K_2HPO_4$, 5 mM $MgSO_4$, 1 mM EGTA, 5 mM creatine, 20 mM glucose, 2 mM $Na_2ATP$, 5 mM pyruvate, and 20 mM taurine, buffered to pH 7.2, Maltsev et al., Circ. Res. 75:233, 1994) and incubated at 37° C. for 15-30 min. Following dissociation cells are seeded into chamber slides and cultured in the differentiation medium to generate single cardiomyocytes capable of beating.

According to still additional preferred embodiments of the present invention, isolating is effected by subjecting the EBs to differentiation factors to thereby induce differentiation of the EBs into lineage specific differentiated cells.

Following is a non-limiting description of a number of procedures and approaches for inducing differentiation of EBs to lineage specific cells.

Neural Precursor Cells

To differentiate the EBs of the present invention into neural precursors, four-day-old EBs are cultured for 5-12 days in tissue culture dishes including DMEM/F-12 medium with 5 mg/ml insulin, 50 mg/ml transferrin, 30 nM selenium chloride, and 5 mg/ml fibronectin (ITSFn medium, Okabe, S. et al., 1996, Mech. Dev. 59: 89-102). The resultant neural precursors can be further transplanted to generate neural cells in vivo (Brüstle, O. et al., 1997. In vitro-generated neural precursors participate in mammalian brain development. Proc. Natl. Acad. Sci. USA. 94: 14809-14814). It will be appreciated that prior to their transplantation, the neural precursors are trypsinized and triturated to single-cell suspensions in the presence of 0.1% DNase.

Oligodendrocytes and Myelinate Cells

EBs of the present invention can differentiate to oligodendrocytes and myelinate cells by culturing the cells in modified SATO medium, i.e., DMEM with bovine serum albumin (BSA), pyruvate, progesterone, putrescine, thyroxine, tri-iodothryonine, insulin, transferrin, sodium selenite, amino acids, neurotrophin 3, ciliary neurotrophic factor and Hepes (Bottenstein, J. E. & Sato, G. H., 1979, Proc. Natl. Acad. Sci. USA 76, 514-517; Raff, M. C., Miller, R. H., & Noble, M., 1983, Nature 303: 390-396]. Briefly, EBs are dissociated using 0.25% Trypsin/EDTA (5 min at 37° C.) and triturated to single cell suspensions. Suspended cells are plated in flasks containing SATO medium supplemented with 5% equine serum and 5% fetal calf serum (FCS). Following 4 days in culture, the flasks are gently shaken to suspend loosely adhering cells (primarily oligodendrocytes), while astrocytes are remained adhering to the flasks and further producing conditioned medium. Primary oligodendrocytes are transferred to new flasks containing SATO medium for additional two days. Following a total of 6 days in culture, oligospheres are either partially dissociated and resuspended in SATO medium for cell transplantation, or completely dissociated and a plated in an oligosphere-conditioned medium which is derived from the previous shaking step [Liu, S. et al., (2000). Embryonic stem cells differentiate into oligodendrocytes and myelinate in culture and after spinal cord transplantation. Proc. Natl. Acad. Sci. USA. 97: 6126-6131].

Mast Cells

For mast cell differentiation, two-week-old EBs of the present invention are transferred to tissue culture dishes including DMEM medium supplemented with 10% FCS, 2 mM L-glutamine, 100 units/ml penicillin, 100 mg/ml streptomycin, 20% (v/v) WEHI-3 cell-conditioned medium and 50 ng/ml recombinant rat stem cell factor (rrSCF, Tsai, M. et al., 2000. In vivo immunological function of mast cells derived from embryonic stem cells: An approach for the rapid analysis of even embryonic lethal mutations in adult mice in vivo. Proc Natl Acad Sci USA. 97: 9186-9190). Cultures are expanded weekly by transferring the cells to new flasks and replacing half of the culture medium.

Hemato-Lymphoid Cells

To generate hemato-lymphoid cells from the EBs of the present invention, 2-3 days-old EBs are transferred to gas-permeable culture dishes in the presence of 7.5% $CO_2$ and 5% $O_2$ using an incubator with adjustable oxygen content. Following 15 days of differentiation, cells are harvested and dissociated by gentle digestion with Collagenase (0.1 unit/mg) and Dispase (0.8 unit/mg), both are available from F.Hoffman-La Roche Ltd, Basel, Switzerland. CD45-positive cells are isolated using anti-CD45 monoclonal antibody (mAb) M1/9.3.4.HL.2 and paramagnetic microbeads (Miltenyi) conjugated to goat anti-rat immunoglobulin as described in Potocnik, A. J. et al., (Immunology Hemato-lymphoid in vivo reconstitution potential of subpopulations derived from in vitro differentiated embryonic stem cells. Proc. Natl. Acad. Sci. USA. 1997, 94: 10295-10300). The isolated CD45-positive cells can be further enriched using a single passage over a MACS column (Miltenyi).

It will be appreciated that the culturing conditions suitable for the differentiation and expansion of the isolated lineage specific cells include various tissue culture medium, growth factors, antibiotic, amino acids and the like and it is within the capability of one skilled in the art to determine which conditions should be applied in order to expand and differentiate particular cell types and/or cell lineages.

In addition to the lineage-specific primary cultures, EBs of the present invention can be used to generate lineage-specific cell lines which are capable of unlimited expansion in culture.

Cell lines of the present invention can be produced by immortalizing the EB-derived cells by methods known in the art, including, for example, expressing a telomerase gene in the cells (Wei, W. et al., 2003. Abolition of Cyclin-Dependent Kinase Inhibitor p16Ink4a and p21Cip1/Waf1 Functions Permits Ras-Induced Anchorage-Independent Growth in Telomerase-Immortalized Human Fibroblasts. Mol Cell Biol. 23: 2859-2870) or co-culturing the cells with NIH 3T3 hph-HOX11 retroviral producer cells (Hawley, R. G. et al., 1994. The HOX11 homeobox-containing gene of human leukemia immortalizes murine hematopoietic precursors. Oncogene 9: 1-12).

To express the telomerase gene in mammalian cells, a polynucleotide encoding telomerase is ligated into an expression vector under the control of a promoter suitable for mammalian cell expression.

The polynucleotide of the present invention is a genomic or complementary polynucleotide sequence which encodes the telomerase gene such as for example, homo sapiens telomerase (GenBank Accession No: NM_003219) or mouse telomerase (GenBank Accession Nos: AF051911, AF073311).

As is mentioned hereinabove, to enable mammalian cell expression, the expression vector of the present invention includes a promoter sequence for directing transcription of the polynucleotide sequence in a mammalian cell in a constitutive or inducible manner.

Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the hypoxia-inducible factor 1 (HIF-1) promoter (Rapisarda, A. et al., 2002. Cancer Res. 62: 4316-24) and the tetracycline-inducible promoter (Srour, M. A. et al., 2003. Thromb. Haemost. 90: 398-405).

The expression vector of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation of the gene of interest (e.g., telomerase). Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I).

Recombinant viral vectors are useful for in vivo expression of the gene of interest (e.g., telomerase) since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of the present invention into stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Since the lineage-specific cells of the present invention are developed by differentiation processes similar to those naturally occurring in the human embryo they can be further used for human cell-based therapy and tissue regeneration.

Thus, according to another aspect of the present invention there is provided a method of treating a disorder requiring cell replacement therapy. The method according to this aspect of the present invention is effected by administering the expanded and/or differentiated lineage-specific cells of the present invention to an individual in need thereof thereby treating the disorder requiring cell replacement therapy.

As used herein "treating a disorder requiring cell replacement therapy" refers to treating an individual suffering from a disorder such as a neurological disorder, a muscular disorder, a cardiovascular disorder, an hematological disorder, a skin disorder, a liver disorder, and the like that require cell replacement.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, "administering" refers to means for providing the expanded and/or differentiated lineage specific cells to an individual, using any suitable route, e.g., oral, sublingual intravenous, subcutaneous, transcutaneous, intramuscular, intracutaneous, intrathecal, intra peritoneal, intra spleenic, intra hepatic, intra pancreatic, intra cardiac, epidural, intraoccular, intracranial, inhalation, rectal, vaginal, and the like administration.

Differentiated stem cells of lineage specific origin can be utilized in treating various disorders. For example, oligodendrocyte precursors can be used to treat myelin disorders (Repair of myelin disease: Strategies and progress in animal models. Molecular Medicine Today. 1997. pp. 554-561), chondrocytes or mesenchymal cells can be used in treatment of bone and cartilage defects (U.S. Pat. No. 4,642,120) and cells of the epithelial lineage can be used in skin regeneration of a wound or burn (U.S. Pat. No. 5,716,411).

For certain disorders, such as genetic disorders in which a specific gene product is missing [e.g., lack of the CFTR gene-product in cystic fibrosis patients (Davies J C, 2002. New therapeutic approaches for cystic fibrosis lung disease. J. R. Soc. Med. 95 Suppl 41:58-67)], ESC-derived cells are preferably manipulated to over-express the mutated gene prior to their administration to the individual. It will be appreciated that for other disorders, the ESC-derived cells should be manipulated to exclude certain genes.

Over-expression or exclusion of genes can be effected using knock-in and/or knock-out constructs.

Knock-out and/or knock-in constructs can be used in somatic and/or germ cells gene therapy to destroy activity of a defective allele, gain of function (e.g., dominant) allele, or to replace the lack of activity of a silent allele in an individual, thereby down or up-regulating activity of specific genes, as required. Further detail relating to the construction and use of knockout and knock-in constructs can be found in Fukushige, S. and Ikeda, J. E.: Trapping of mammalian promoters by Cre-lox site-specific recombination. DNA Res 3 (1996) 73-50; Bedell, M. A., Jerkins, N. A. and Copeland, N. G.: Mouse models of human disease. Part I: Techniques and resources for genetic analysis in mice. Genes and Development 11 (1997) 1-11; Bermingham, J. J., Scherer, S. S., O'Connell, S., Arroyo, E., Kalla, K. A., Powell, F. L. and Rosenfeld, M. G.: Tst-1/Oct-6/SCIP regulates a unique step in peripheral myelination and is required for normal respiration. Genes Dev 10 (1996) 1751-62, which are incorporated herein by reference.

In addition to cell replacement therapy, the lineage specific cells of the present invention can also be utilized to prepare a cDNA library. mRNA is prepared by standard techniques from the lineage specific cells and is further reverse transcribed to form cDNA. The cDNA preparation can be subtracted with nucleotides from embryonic fibroblasts and other cells of undesired specificity, to produce a subtracted cDNA library by techniques known in the art.

The lineage specific cells of the present invention can be used to screen for factors (such as small molecule drugs, peptides, polynucleotides, and the like) or conditions (such as culture conditions or manipulation) that affect the differentiation of lineage precursor to terminally differentiated cells. For example, growth affecting substances, toxins or potential differentiation factors can be tested by their addition to the culture medium.

While reducing the present invention to practice, the present inventors have uncovered that the culturing conditions described above (e.g., use of bioreactor which maintains cells in a state of free fall) can also be utilized to expand ESC lines.

As is well known in the art, ESCs can be maintained in a proliferative, undifferentiated state using feeder-based or feeder-free systems. However, for many applications, such as tissue regeneration and cell-based therapy, large quantities of undifferentiated cells are needed. Attempts to generate large quantities of ESCs using prior art feeder-based or feeder-free systems resulted in formation of ESC clumps which limit the expansion capacity of such systems.

Thus, according to another aspect of the present invention there is provided a method of dynamically expanding ESCs under nondifferentiating conditions.

The method is effected by seeding ESCs at a concentration of $0.5-1.5 \times 10^6$ cells/ml in a rotating cell culture system (RCCS) or preferably the STLV bioreactor (available from Synthecon™ Inc, Cellon S.A. Bereldange, Luxembourg) which includes 55 ml of undifferentiated culture medium such as mouse embryonic fibroblasts (MEF) conditioned medium, foreskin conditioned medium, or a more defined medium including 85% KO-DMEM, 15% serum replacement, 2 mM L-glutamine, 0.1 M β-mercaptoethanol, 1% non-essential amino acids, 0.12 ng/ml TGFβ$_1$, 1000 u/ml LIF and 4 ng/ml bFGF. Culturing is effected by horizontally rotating the bioreactor round a longitudinal axis at a rotational speed of 10-20 rpm in a microgravitational environment of 0.1 G. The culturing period varies between 3-30 days, depending on the degree of expansion required.

ESCs cultured under such conditions are subjected to low shear forces, microgravity and a state of free fall, which enable a control over the agglomeration process. Under such conditions, the process of ESC expansion can be scaled up to produce large quantities of undifferentiated ESCs.

It will be appreciated that ESCs can be attached to specific carriers such as scaffolds or beads coated with a specific matrix which is capable of supporting the growth of ESCs. The scaffolds or beads used by the present invention can be natural or synthetic, with different degrees of porosity and biodegradability [Pei M et al., 2002. Bioreactors mediate the effectiveness of tissue engineering scaffolds. FASEB J. 16(12):1691-4; Botchwey E A et al., 2001. Bone tissue engineering in a rotating bioreactor using a microcarrier matrix system. J Biomed Mater Res. 55(2): 242-53; Gonda S R et al., 2001. Three-dimensional transgenic cell model to quantify genotoxic effects of space environment. Adv Space Res. 27(2): 421-30.; Torgan C E et al., 2000. Differentiation of mammalian skeletal muscle cells cultured on microcarrier beads in a rotating cell culture system. 38(5): 583-90; Lelkes P I et al., 1998. Simulated microgravity conditions enhance differentiation of cultured PC12 cells towards the neuroendocrine phenotype. In Vitro Cell Dev Biol Anim. 34(4): 316-25; Hammond T G, and Hammond J M. 2001. Optimized suspension culture: the rotating-wall vessel. Am J Physiol Renal Physiol. 281(1): F12-25].

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al., (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al., (Eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); "Teratocarcinomas and Embryonic Stem Cells: A Practical Approach" Robertson E J, ed. (1987)Oxford: IRL Press; "Manipulating the Mouse Embryo" Nagy A et al.,(2003) Cold Spring Harbor Lab Press, Third Edition; Thomson, J. A., Marshall, V. S. (1998) Primate embryonic stem cells. Current Topics in Developmental Biology 38, 133-165; Marshall, V. S., Waknitz, M. A., Thomson, J. A. (2001) Isolation and maintenance of primate embryonic stem cells. Methods in Molecular Biology 158, 11-18; all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below Example 1

Dynamic Culture of Human Embryonic Stem Cells for the Formation of Human Embryoid Bodies According to the current practice, the formation of embryonic bodies (EBs) involves the aggregation of multiple hES cells via a static growth of ES cultures, a procedure which results in large aggregates with necrotic centers. The following example illustrates a novel approach for dynamically generating hEBs thereby allowing large-scale production of small-size EBs suitable for therapeutic applications.

Materials and Methods:

Human ES Cell cultures—Undifferentiating hESCs [H9.2 passages 36-60 (Amit et al., 2000)] were grown on an inactivated mouse embryonic feeder layer (MEF) with culture medium consisting of 80% knockout (KO) DMEM (Gibco-Invitrogen Co.) supplemented with 20% (v/v) defined fetal bovine serum (FBSd; HyClone, Utah, USA), 1 mM L-glutamine, 0.1 mM mercaptoethanol, and 1% non-essential amino acid stock (all from Gibco-Invitrogen Co.). The hESCs were fed daily with fresh medium and were passaged every 4-7 days using 0.1% type IV Collagenase solution and 30 minutes incubation. Collagenase treatment resulted in small aggregates, which were re-seeded on freshly prepared feeder layers.

Induction of differentiation of hES cells—To induce differentiation, confluent six-well plates (60 cm$^2$) of undifferentiated hESCs were used. The hESCs were dispersed into small clumps (3-20 cells) using 0.5 mM EDTA supplemented with 1% FBS (HyClone, Utah, USA). Differentiation of ES cells into EBs was in the presence of a tissue culture medium consisting of 80% KO-DMEM, 20% FBSd, 0.5% Penicillin-Streptomycin (Sigma-Aldrich Corp., St Louis, Mo., USA), 1 mM L-glutamine, 0.1 mM β-mercaptoethanol, and 1% non-essential amino acid stock (all from Gibco Invitrogen Co.).

EBs culturing systems—The effect of dynamic culture on EB formation was assessed in the rotating cell culture systems (RCCS), developed by NASA. RCCS are horizontally rotated, fluid-filled culture vessels equipped with membrane diffusion gas exchange to optimize gas/oxygen-supply. In RCCS, the operating principles are: (i) whole body horizontal rotation which is characterized by extremely low fluid shear stress and (ii) oxygenation by active or passive diffusion to the exclusion of all but dissolved gasses from the reactor chamber, yielding a vessel devoid of gas bubbles and gas/fluid interfaces (Lelkes and Unsworth, 2002). The resultant flow pattern within the RCCS is laminar, with mild mixing, since the rotation of the vessel is slow. The settling of the cell clusters, which is associated with oscillations and tumbling, generates fluid mixing. The outcome is a very low shear environment. Another advantage of the RCCS is that they are geometrically designed so that the membrane area to volume of medium ratio is high, thus enabling efficient gas exchange.

Two types of rotating bioreactors were examined: the Slow Turning Lateral Vessel (STLV, FIG. 1a) and the High Aspect Ratio Vessel (HARV, FIG. 1b). The STLV is tubular shaped chamber with a central gas transfer cord, while the HARV has a disc shaped culture chamber with the oxygenator membrane forming the inside wall of the vessel.

Human EBs were formed in the following suspension cultures: (i) 60 mm Petri dishes (Miniplast, Ein Shemer, Israel) with 10 ml medium for static culture; (ii) 55 ml STLV; and (iii) 10 ml or 50 ml HARV, both purchased from Synthecon™ Inc, Cellon S.A. Bereldange, Luxembourg. The hESCs were seeded into the vessels at initial cell concentrations ranging from $(0.1\text{-}1.2) \times 10^6$ cells per 1 ml medium. The bioreactors were set to rotate at a speed in which the suspended cell aggregates remained close to a stationary point within the reactor vessel.

Evaluation of size and numbers of EBs—Two samples of 1 ml each, including medium and 7, 14 and 21 day-old hEBs from all culture systems were transferred into culture dishes and analyzed using an inverted-light microscopy (Olympus). In each system, the counts of total hEBs from 5 fields of a 100-times magnification were averaged. For size analysis, the diameter average was calculated by measuring the large and small diagonals of 5 representative hEBs from each field. The results of measurements from two independent experiments are presented.

Histology analysis—For histology analysis, 7 day and 30 day-old hEBs were fixed in 10% neutral-buffered formalin, dehydrated in graduated alcohol (70%-100%), and embedded in paraffin. Histological slides were prepared by staining 1-5 μm sections with Hematoxylin-Eosin (H&E) stains.

Experimental Results

Human EB formation in the rotating bioreactors—To examine the suitability of the RCCS systems as milder bioreactors for hEB formation and differentiation, undifferentiating hESCs were removed from their feeder layers and transferred to suspension cultures in the 55 ml STLV system, the 10 ml or 50 ml HARV system or the conventional static petri dishes. The cells were inoculated into the different cultures at different initial concentrations, ranging from $(0.1\text{-}1.2) \times 10^6$ cells per ml, in aim to find the optimal conditions for cell aggregation. The goal was to increase the number of formed EBs per a given cell density inoculum.

Formation of cell aggregates—When seeded with low cell concentrations, i.e., $(0.1\text{-}0.25) \times 10^6$ cells/ml, no cell aggregates were formed up to 24 hours following seeding; the cells at this time point appeared dead according to the trypan blue dye exclusion assay (data not shown). Attempts to increase cell aggregation in the rotating cultures by minimizing the rotation speed to ≦13 rpm did not result in cell aggregation. At high cell density inoculum of more than $1 \times 10^6$ cells/ml, the cells aggregated into big clumps within hours after seeding and increasing vessel rotation to 25-30 rpm did not affect the process. Efficient cell aggregation, i.e., the formation of a large number of small aggregates following 12-24 hours, was achieved in the STLV rotating vessel when seeded with $(0.5\text{-}0.7) \times 10^6$ cells/ml and at a rotation speed of 15-20 rpm. On the other hand, when these conditions were employed using the HARV bioreactor, large cell clumps were formed (calibration data are not shown).

A close examination under a light microscope of the STLV-formed hEBs following one month of cultivation revealed relatively homogenous small aggregates (their diameter ranging between 400-800 μm) with some cystic hEBs, as shown in FIG. 2a. In contrast, 2-5 large cell clumps (ranging between 600-1800 μm) with extensive necrotic areas were found in the one-month old HARV cultures (FIG. 2b). In addition, hEBs formed in the conventional static cultures exhibited extensive agglomeration of the hEBs, although to a lesser extent than in the HARV bioreactor (FIG. 2c).

Thus, these results demonstrate that the STLV bioreactor is suitable for efficient cell aggregation which is a prerequisite for efficient EB formation.

Example 2

EB Formation is More Efficient in the STLV Bioreactor Than in Static Cultures

To examine the efficiency of hEBs formation using the STLV bioreactor the number of hEBs and the DNA and protein contents were determined.

Materials and Methods

Medium sampling and analysis—Human ESCs were cultured using either the STLV bioreactor or the static cultures. Every third-fifth day 70% of the medium was replaced according to manufacture instructions. Shortly, vessels were stopped and aggregates were allowed to settle down. Triplicate samples from the medium were immediately analyzed for $pO_2$, $pCO_2$, pH, glucose and lactic acid levels using Blood Gas Analyzer, (StatProfile M, Nova Biomedical, Boston) or stored at −70° C. for analysis of lactate dehydrogenase (LDH) activity (Hitachi Modular P800, Tokyo, Japan). Glucose consumption at a given time point was determined from the medium concentration of glucose taking into account the 70% volume replacement of the medium.

Biochemical Assays—At different times in culture, the vessels were stopped and 6% of the cell suspension volume in the vessel was removed for biochemical analyses. To ensure homogenous sampling of the cell suspensions, a vigorous mixing was performed before sampling and the volume collected each time was 2%. EBs were collected after settling down and were analyzed for DNA and cell viability. The experiments were performed in triplicates. For total protein, EBs pellets were collected at days 7 and 28, and stored at −70° C. until analysis.

DNA content was measured (n=3) using Hoechst 33258 dye (Sigma, St. Louis Mo., USA) and calf thymus DNA (Type 1, Sigma) as a standard. Briefly, 2 µg/ml Hoechst 33258 dye was added to the EBs sample. Following 10 minutes of incubation, the cell pellets were transferred to 96-well plates containing 150 µl with no dye. The plate was read in a microplate reader (Ceres UV900, Bio-Tek, Winooski, Vt., USA) at 340 nm.

The concentration of viable cells was calculated from the spectrophotometric measurements of the conversion of XTT to a water-soluble colored formazan derivative at a wavelength of 450 nm (Cat No. TOX-2, Sigma, St. Louis Mo., USA) according to manufacturer's instructions. Briefly, EBs were incubated for 4 hours with medium containing 20% (v/v) XTT solution. For analysis, 150 µl of the medium were removed, placed in a 96-well plates and was read in microplate reader at 450 nm.

Cell concentration was determined from a standard curve of known cell concentrations. EBs were lysed using a lysis buffer according to manufacturer's instructions (R&D systems, Inc. Minneapolis, Minn., USA) and total protein was measured in triplicates using the BCA Protein assay (Pierce, Technology Corporation, New York, N.Y., USA) according to manufacturer's instructions.

Statistical Analysis—The MIXED algorithm of the SAS package (Statistical Analysis System) was used in order to take into account time-correlation within a given system. The dependence on time was first modeled as a parabola. However, except for LDH leakage assay, in all other parameters the quadratic coefficient was found insignificant and therefore a linear trend was used (data are graphically displayed with the fitted model). Time dependence was modeled as a first order autoregressive structure to account for the errors. Fitted regression coefficients test of the significance of the differences was used for comparison of systems.

Staining for dead cells and apoptosis—The presence of dead cells in hEBs was evaluated using the Ethidium homodimer-1 (EthD-1; Molecular Probes, Inc., Eugene, Oreg., USA) dye according to manufacturer's instructions. Briefly, one-month-old hEBs were allowed to attach on cover slips for 48 hours, then washed twice with PBS (Gibco) and incubated with 4 µM EthD-1 for 45 minutes at room temperature. Samples were analyzed using a confocal microscopy (Bio-Rad, Laboratories Ltd. Hertfotdshire, England) at Excitation of 495 nm and Emission of 635 nm.

Tunnel assay (Roche, Basel, Switzerland) was performed to identify DNA strand breaks labeled with fluorescein in the hEBs, according to manufacturer's instructions. Briefly, one-month-old hEBs were fixed in 10% neutral-buffered formalin, dehydrated in graduated alcohol (70%-100%), embedded in paraffin and sectioned. After removal of the paraffin, slides were incubated for 30 min with 0.1% Triton X-100 in 0.1% sodium citrate (all from Sigma), rinsed twice with PBS (Gibco) and air-dried. Tunnel reaction mixture (50 µl per slide) was added and slides were incubated for 60 minutes at 37° C., following which slides were rinsed three times in PBS (Gibco). For negative control of auto-fluorescence, deparaffinized slides were used. Samples were analyzed under a fluorescence microscope (IX50 inverted system microscopy Olympus Optical Co., LTD. Tokyo, Japan) using an excitation wavelength in the range of 450-500 nm and detection in the range of 515-565 nm.

Experimental and Statistical Results

STLV cultures contain more EBs exhibiting smaller sizes as compared with static cultures—EBs formation was evaluated using an inverted light microscope following one and two weeks in culture. As is shown in FIGS. 3a-d, while the STLV cultures included multiple, small size—EBs, the static cultures included large cysts and adhered EBs. A quantification analysis revealed that seven days post seeding of hESCs the number of EBs in the STLV cultures (7.7±1.8/ml; n=3) was nearly 4 times higher than the number of EBs in the static cultures (2±0.6/ml; n=3). In addition, when EBs diameter was compared it was found that the STLV-formed EBs were smaller than the static culture-formed EBs (20±7 vs. 140±90 µm, respectively). Noteworthy is that from day seven thereafter, the number of EBs did not change significantly in both cultures, but their size increased with time. The one-month-old hEBs reached the size of 400-800 and 400-1200 µm in diameter, in the STLV and the static culture, respectively.

STLV cultures contain more DNA and protein than the static cultures—In order to assess culture cellularity the total protein and DNA contents in the STLV and the static cultures were quantified. As is shown in FIGS. 3e-h, following one cultivation week a similar two-fold increase of DNA and protein contents was detected in both systems. From the second week thereafter, the increase in protein and DNA content was much more significant in the STLV system as compared with the static culture. Following 28 days in culture, the total protein concentration was nearly 3-fold higher in the STLV culture than in the static petri dish culture (27.916±0.960 µg/ml (n=3) versus 10.713±0.379 µg/ml (n=3), respectively). Similarly, the DNA concentration was nearly 3-fold higher in the STLV culture than in the static culture, (51.273±0.464 mg/ml (n=3) versus 18.958±0.816 mg/ml (n=3), respectively). Translation of the protein and DNA concentration data into cell concentration using the appropriate calibration curves (Tables 1 and 2, hereinbelow) revealed that on day 28 in culture the calculated cell concentrations were $36 \times 10^6$ cells/ml in the STLV culture and $13 \times 10^6$ in the static culture. These data correspond to 70-fold and 25-fold increase in cell concentration compared to initial cell seeding values for the STLV and the static cultures, respectively.

TABLE 1

Extrapolation of DNA concentration to cell concentration

| | STLV | | Static | |
|---|---|---|---|---|
| Days in culture | DNA (mg/ml) ± SD | Cells ($\times 10^6$/ml) | DNA (mg/ml) ± SD | Cells ($\times 10^6$/ml) |
| 0 | 1.369 ± 0.294 | 0.5 | 1.369 ± 0.294 | 0.5 |
| 7 | 4.596 ± 0.025 | 2.875 | 3.849 ± 0.0009 | 2.338 |
| 14 | 8.253 ± 0.082 | 5.501 | 5.568 ± 0.1231 | 3.572 |
| 21 | 21.798 ± 0.434 | 15.228 | 12.639 ± 0.162 | 8.651 |
| 28 | 51.273 ± 0.464 | 36.395 | 18.958 ± 0.816 | 13.188 |

Table 1: DNA concentration was calculated from the equation y = 0.0002X + 0.0127 ($R^2$ = 0.985) which was generated using a standard curve; Cell concentration was calculated from the equation y = 0.2785X + 0.1313 ($R^2$ = 0.9907).

TABLE 2

Extrapolation of protein concentration to cell concentration

| | STLV | | Static | |
|---|---|---|---|---|
| Days in culture | DNA (µg/ml) ± SD | Cells ($\times 10^6$/ml) | DNA (µg/ml) ± SD | Cells ($\times 10^6$/ml) |
| 0 | 1.593 ± 0.028 | 0.5 | 1.592 ± 0.028 | 0.5 |
| 7 | 2.247 ± 0.310 | 1.652 | 2.582 ± 0.065 | 1.882 |
| 28 | 27.916 ± 0.960 | 37.217 | 10.713 ± 0.379 | 13.222 |

Table 2: Protein concentration was calculated from standard curve using the equation y = 0.2989X − 0.3545 ($R^2$ = 0.9626); Cell concentration was calculated from the equation y = 0.2143X − 0.014 ($R^2$ = 0.9556).

Increased cell viability in STLV cultures—To assess ES-derived cell viability during hEBs formation the culturing medium was assayed for XTT viability. In the static petri dish culture, the XTT assay revealed a two-fold increase in viable cell concentration within the first week of cultivation, while in the STLV culture no significance increase was observed compared to the initial seeding value (Table 3, hereinbelow). The two-fold increase in viable cell concentration in the static culture agrees with the increase in culture cellularity as determined by the DNA and protein contents (FIGS. 3e-h). The discrepancy in the STLV system can be explained by cell death during the first cultivation week due to the mixing conditions in the vessel since hESCs are sensitive to even a mild mixing as in the STLV system. On the other hand, from the second week in culture, the concentrations of viable cells increased in the STLV system and from the third week in culture the cell concentration exceeded that observed in the static culture (FIGS. 4a-d). On day 28 in culture, the viable cell concentration in the STLV culture reached the value of $35 \times 10^6$ cells/ml (Table 3, hereinbelow), in agreement with the value determined by the DNA and protein contents (Tables 1 and 2, respectively, hereinabove). On the other hand, in the static petri dish culture, starting from the second week in culture there is a moderate increase in viable cell concentration probably as a result of extensive cell death in the growing hEBs.

TABLE 3

Extrapolation of viability to cell concentration in Ebs

| Day in culture | STLV Cells ($10^6$/ml) | Static Cells ($10^6$/ml) |
|---|---|---|
| 0 | 0.5 | 0.5 |
| 7 | 0.501 | 1.212 |
| 14 | 4.126 | 3.242 |
| 21 | 14.613 | 7.398 |
| 28 | 35.741 | 10.884 |

Table 3: Cell concentration was calculated from the equation y = 0.1357X + 0.017 which was generated using a standard curve.

To further evaluate cell viability in EBs cultures the LDH leakage was measured in the culturing medium during EBs cultivation. In the STLV system, the high levels of LDH were detected during the first cultivation week, however, LDH levels progressively decreased throughout the culture. The initial high LDH activity in the STLV cultures was 60% higher than the in the static culture. On the other hand, in the static culture, LDH activity was increased starting from the second week in culture. These results are in agreement with the increase in hEBs size due to some agglomeration events detected in the static cultures (see FIGS. 3a-d).

Increased apoptosis and necrosis events in EBs generated using the static cultures—To evaluate the degree of cell death within the hEBs, one-month-old hEBs were stained using the EthD-1 staining. As is shown in FIGS. 4e-h, while no significant staining was detected in STLV-formed EBs, a positive staining was observed in static culture-formed EBs, indicating the presence of dead cells in these cultures. To further evaluate the involvement of apoptosis and/or necrosis events in cell death within the EBs, a Tunnel assay, which labels DNA breaks, was employed. As is seen in FIGS. 4i-l, while some DNA fragmentation was detected in one-month-old static culture-formed EBs, no DNA fragmentation was detected in one-month-old STLV-formed EBs.

Medium Metabolic Parameters—To further evaluate the suitability of the STLV system to support normal rate of proliferation and differentiation of hESCs into hEBs, the medium metabolite parameters of the EBs cultures were measured. As is seen in FIGS. 5a-b, while in the STLV cultures glucose consumption increased along with culture time, in the static cultures glucose consumption decreased. The decrease in glucose consumption in the static cultures, can be explained by the extent of cell differentiation in relation to cell proliferation in these cultures since differentiating cells consume less glucose than the proliferating ESCs. In addition, the slight increase in lactic acid production and increase in medium acidity observed in the STLV cultures but not in the static cultures suggest the promotion of extensive cell proliferation and differentiation using the STLV system (FIGS. 5c-d). On the other hand, in both the static culture and the STLV culture, the concentration of oxygen and $CO_2$ were maintained at physiological levels during cultivation (FIGS. 5e and 5f, respectively).

Altogether, these results demonstrate that following one month in culture more viable and less dead cells are found in STLV-formed EBs as compared with the static culture-formed EBs. In addition, the medium metabolite parameters such as lactic acid and acidity demonstrate pronounced proliferation along with the differentiation of hEBs in the STLV cultures. These results further suggest the use of the STLV system for generating large quantities of viable hEBs.

Example 3

The STLV Bioreactor is Suitable for EB Differentiation

To further examine the suitability of the STLV and HARV bioreactors to support EB differentiation, one-month-old EBs were subjected to histological staining, immunohistochemistry and RT-PCR analyses.

Materials and Methods

Immunohistochemistry—Immunostaining was preformed following deparaffinization of histological sections using the Dako LSAB®+ staining kit for anti glial fibrillary acidic protein (GFAP), anti CD34 and somatostatin (all from Dako Corp, Carpenteria, Calif., USA) according to manufacturer's instructions. Both IgG isotypes and secondary antibody staining were used as controls.

Reverse transcription (RT)-PCR analysis—Total RNA was extracted from hEBs using the TriReagent (Sigma) according to manufacturer's instructions. To ensure no DNA contamination, RNA samples were treated with DNA free kit (Ambion Inc., Austin, Tex., USA) and examined for DNA contamination prior to performing the RT reaction. The total RNA was quantified via UV spectrophotometry and 1 µg of RNA was used for each RT reaction in a final volume of 20 µl. RNA was reversed transcribed using M-MLV (Promega Corp., Madison, Wis., USA) and oligo (dT) primers (Promega Co., Madison, Wis., USA) according to manufacturer's instructions. PCRs reactions were performed on 1 µl of the product from the RT reaction using the BIOTAQ™ DNA Polymerase (Bioline Ltd. UK) according to manufacturer's instructions. To ensure semi quantitative RT-PCR assay results, $MgCl_2$ concentration and the number of PCR cycles were adjusted for each set of primers so as to ensure unified amplification. In addition, all RNA samples were adjusted according to amplification of GAPDH, which was used as a normalizing standard for each sample.

PCR primers and reaction conditions are shown in Table 4 hereinbelow. PCR reaction conditions were as follows: 5 minutes at 94° C. (hot start), 30-40 cycles (actual number described in Table 4) of: 94° C. for 30 seconds, annealing temperature (as in Table 4) for 30 sec, 72° C. for 30 sec. A final 7-min extension at 72° C. was performed at the end.

TABLE 4

PCR primers and condition

| Gene product (Accession number) | SEQ ID NOs. | Forward (F) and reverse (R) primers (5'→3') | Reaction Condition | Size (bp) |
|---|---|---|---|---|
| Neurofilament 68 KD (AY156690) | SEQ ID NO: 1<br>SEQ ID NO: 2 | F: GAGTGAAATGGCACGATACCTA<br>R: TTTCCTCTGCCTTCTTCACCTTC | 35 cycles, annealing at 60° C., in 1.5 mM $MgCl_2$ | 473 |
| CK10 (XM_352919) | SEQ ID NO: 3<br>SEQ ID NO: 4 | F: GCTGACCTGGAGATGCAAATTGAGAGCC<br>R: GGGCAGCATTCATTTCCACATTCACATCAC | 35 cycles annealing at 65° C., in 1.5 mM $MgCl_2$ | 129 |
| α-cardiac actin (NM_005159) | SEQ ID NO: 5<br>SEQ ID NO: 6 | F: GGAGTTATGGTGGGTATGGGTC<br>R: AGTGGTGACAAAGGAGTAGCCA | 35 cycles, annealing at 65° C., in 2.0 mM $MgCl_2$ | 468 |
| CMP (NM_002379) | SEQ ID NO: 7<br>SEQ ID NO: 8 | F: ATGACTGTGAGCAGGTGTGC<br>R: GTCCAGCGTATCCACGATCT | 35 cycles, annealing at 55° C., in 1.5 mM $MgCl_2$ | 224 |
| Albumin (AF542069) | SEQ ID NO: 9<br>SEQ ID NO: 10 | F: TGCTTGAATGTGCTGATGACAGGG<br>R: AAGGCAAGTCAGCAGCCATCTCAT | 35 cycles, annealing at 60° C., in 1.5 mM $MgCl_2$ | 157 |
| α-fetoprotein (BC027881) | SEQ ID NO: 11<br>SEQ ID NO: 12 | F: GCTGGATTGTCTGCAGGATGGGAA<br>R: TCCCCTGAAGAAAATTGGTTAAAAT | 35 cycles, annealing at 60° C., in 1.5 mM $MgCl_2$ | 216 |
| GATA 4 (NM_002052) | SEQ ID NO: 13<br>SEQ ID NO: 14 | F: AGACATCGCACTGACTGAGAAC<br>R: GACGGGTCACTATCTGTGCAAC | 35 cycles, annealing at 60° C., in 1.0 mM $MgCl_2$ | 475 |
| Oct4 (S81255) | SEQ ID NO: 15<br>SEQ ID NO: 16 | F: GAGAACAATGAGAACCTTGAGGAGA<br>R: TTCTGGCGCCGGTTACAGAACCA | 32 cycles, annealing at 60° C., in 1.0 mM $MgCl_2$ | 219 |
| Renin (AY436324) | SEQ ID NO: 17<br>SEQ ID NO: 18 | F: GTGTCTGTGGGGTCATCC<br>R: ATCAAACAGCCTCTTCTTGGC | 32 cycles annealing at 65° C., in 1.5 mM $MgCl_2$ | 142 |
| CD31 (NM_000442) | SEQ ID NO: 19<br>SEQ ID NO: 20 | F: CAACGAGAAAATGTCAGA<br>R: GGAGCCTTCCGTTCTAGAGT | 32 cycles, annealing at 60° C., in 1.5 mM $MgCl_2$ | 260 |
| GAPDH (J04038) | SEQ ID NO: 21<br>SEQ ID NO: 22 | F: AGCCACATCGCTCAGACACC<br>R: GTACTCAGCGCCAGCATCG | 32 cycles, annealing at 60° C., in 1.5 mM $MgCl_2$ | 302 |

Experimental Results

Figure 6E:
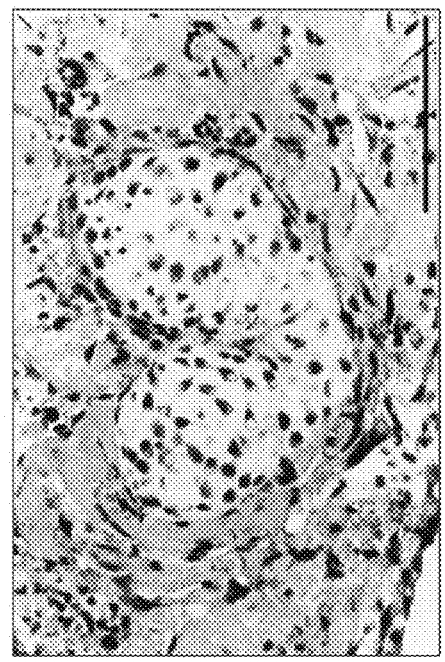

EBs generated using the STLV bioreactor differentiated into complex structures—Sections of one-month-old EBs generated using the STLV or static cultures were prepared for histological analyses using Hematoxylin-Eosin staining. As is shown in FIGS. 6a-f, while a progressive differentiation was observed in EBs generated using the STLV bioreactor, including the formation of complex structures such as epithelial neuronal tubes (FIG. 6a), blood vessels (FIG. 6b) and glands (FIG. 6c), the HARV cultures included large clumps with pronounced necrotic areas (FIG. 6d), and the development of differentiated structures could be observed mainly in the clumps' edges (FIGS. 6e-f).

These results demonstrate that EBs generated using the STLV bioreactor include all three embryonic germ layers and as such are an excellent source of ESC-derived-differentiated cells.

EBs generated using the STLV bioreactor express differentiation-specific markers of all three embryonic germ layers—To further determine the extent of differentiation in the STLV-formed EBs, histological sections of one-month-old hEBs were subjected to immunohistochemistry analysis. As is shown in FIGS. 7a-c, STLV-formed EBs expressed the glial fibrillary acidic protein (GFAP) in the neuronal tubes (FIG. 7a), the CD34 hematopoietic marker in cells surrounding the blood vessels (FIG. 7b) and the somatostatin production in endodermal structures (FIG. 7c), all of which correspond to the embryonic ectoderm, mesoderm and endoderm origins, respectively.

The expression of representative genes of each of the three germ layers was further analyzed using semi-quantitative RT-PCR reactions. As is shown in FIG. 7d, hEBs generated using both the STLV and the static cultures expressed a variety of genes representative of all three embryonic germ layers. These included the neurofilament 68 KD (NF) and cytokeratin 10 (CK10) which represent the ectoderm layer, α-cardiac actin (α-CA), renin, cartilage matrix protein (CMP) and CD31, which represent the mesoderm and albumin, ectoderm α-fetoprotein, and transcription factor GATA4 which represent the endoderm. In addition to the differentiation markers, the expression level of the embryonic transcription factor Oct4, a marker of undifferentiated ESCs, and the house keeping gene GAPDH was also determined. As is further shown in FIG. 7d, the expression of Oct4 was relatively high at day 7 of EB cultures and significantly decreased by day 30 of culture. On the other hand, the expression level of all the differentiation markers examined was relatively high and persisted throughout the culture period.

Thus, these results demonstrate the progression of differentiation in hEBs developed using either the STLV bioreactor or the static petri dish cultures.

Altogether, the results presented in Examples 1-3 of the present invention demonstrate that the STLV bioreactor provides a culturing environment which is suitable for the normal formation and proliferation of hEBs by enabling optimal control over the agglomeration process of hEBs. Furthermore, cultivation of hESC in the STLV system yields three-fold more hEBs particles as compared to conventional static cultivation in petri dishes, thus making the present approach highly suitable for applications requiring large amounts of stem cells.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

REFERENCES CITED

Additional References are Cited in the Text

1. Amit M, Carpenter M K, Inokuma M S, Chiu C P, Harris C P, Waknitz M A, Itskovitz-Eldor J, Thomson J A. 2000. Clonally derived human embryonic stem cell lines maintain pluripotency and proliferative potential for prolonged periods of culture. Dev Biol 227:271-278.
2. Chisti Y. 2001. Hydrodynamic damage to animal cells. Crit Rev Biotechnol 21:67-110.
3. Dang S M, Kyba M, Perlingeiro R, Daley G Q, Zandstra P W. 2002. Efficiency of embryoid body formation and hematopoietic development from embryonic stem cells in different culture systems. Biotechnol Bioeng 78:442-453.
4. Hammond T, Hammond J M. 2001. Optimized suspension culture: the rotating-wall vessel. Am J Physiol Renal Physiol 281:F12-F25.
5. Itskovitz-Eldor J, Schuldiner M, Karsenti D, Eden A, Yanuka 0, Amit M, Soreq H, Benvenisty N. 2000. Differentiation of human embryonic stem cells into embryoid bodies compromising the three embryonic germ layers. Mol Med 6:88-95.
6. Lelkes P I, Galvan D L, Hayman G T, Goodwin T J, Chatman D Y, Cherian S, Garcia R M, Unsworth B R. 1998. Simulated microgravity conditions enhance differentiation of cultured PC12 cells towards the neuroendocrine phenotype. In Vitro Cell Dev Biol Anim. 34:316-25.
7. Lelkes P I, Unsworth B R. 2002. Neuroectodermal cell culture: endocrine cells. In: Atala A, Lanza R P, editors. Methods of tissue engineering. London: Academic Press. P 371-382.
8. Reubinoff B E, Pera M F, Fong C Y, Trounson A, Bongso A. 2000. Embryonic stem cell lines from human blastocysts: somatic differentiation in vitro. Nat Biotechnol 18:399-404.
9. Thomson J A, Itskovitz-Eldor J, Shapiro S S, Waknitz M A, Swiergiel J J, Marshall V S, Jones J M. 1998. Embryonic stem cell lines derived from human blastocysts. Science 282:1145-1147.
10. Unsworth B M, Lelkes P I. 1998. Growing tissues in microgravity. Nat Med 4:901-907.
11. Wartenberg M, Donmez F, Ling F C, Acker H, Hescheler J, Sauer H. 2001. Tumor-induced angiogenesis studied in confrontation cultures of multicellular tumor spheroids and embryoid bodies grown from pluripotent embryonic stem cells. FASEB J 15:995-1005.
12. Wolf D A, Schwarz R P. 1991. Analysis of gravity-induced particle motion and fluid perfusion flow in the NASA-designed rotating zero-head-space tissue culture vessel. NASA Technical paper 3134.

What is claimed is:

1. A method of dynamically generating embryoid bodies comprising culturing embryonic stem cells in slow turning lateral vessel bioreactor which subjects cells cultured in a fluid contained therein to randomized gravity vectors without formation of gas bubbles in said fluid to thereby obtain dynamically generated embryoid bodies.

2. The method of claim 1, wherein said bioreactor exerts a microgravitational force on said embryonic stem cells selected from the range of 0.05-0.9 G on said cells cultured therein.

3. The method of claim 2, wherein said microgravitational force is 0.1 G.

4. The method of claim 1, wherein said bioreactor maintains said embryonic stem cells in a state of free fall.

5. The method of claim 1, wherein said bioreactor holds a fluid volume selected from the range of 1-500 ml.

6. The method of claim 1, wherein a diameter of said bioreactor is selected from range of 2.54-15.24 centimeters.

7. The method of claim 6, wherein said culturing of said embryonic stem cells is effected in said bioreactor under a rotational speed selected from a range of 15-20 rpm.

8. The method of claim 1, wherein said bioreactor enables oxygenation of said fluid via controlled diffusion of dissolved gasses.

9. The method of claim 1, wherein said embryonic stem cells are cultured at an initial concentration of $0.5\text{-}0.7 \times 10^6$ cells per milliliter medium.

10. The method of claim 1, wherein said culturing of said embryonic stem cells is effected in a culture medium selected as being suitable for embryoid bodies formation.

11. The method of claim 10, wherein said culture medium includes 80% DMEM, 20% serum, 0.5% Penicillin-Streptomycin, 1 mM L-glutamine, 0.1 mM β-mercaptoethanol and 1% non-essential amino acid stock.

12. The method of claim 1, wherein said culturing is effected over a culturing period of 1-35 days.

13. The method of claim 1, wherein said culturing is effected for 30 days.

* * * * *